(12) United States Patent
Havasi et al.

(10) Patent No.: US 9,238,621 B2
(45) Date of Patent: Jan. 19, 2016

(54) PROCESSES FOR THE PREPARATION OF PROSTAGLANDIN AMIDES

(75) Inventors: Gábor Havasi, Budapest (HU); Tibor Kiss, Budapest (HU); Irén Hortobágyi, Budapest (HU); Zsuzsanna Kardos, Budapest (HU); István Lászlófi, Budapest (HU); Zoltán Bischof, Budapest (HU); Ádám Bódis, Budapest (HU)

(73) Assignee: CHINOIN ZRT, Budapest (HU)

( * ) Notice: Subject to any disclaimer, the term of this patent is extended or adjusted under 35 U.S.C. 154(b) by 0 days.

(21) Appl. No.: 14/123,497

(22) PCT Filed: May 25, 2012

(86) PCT No.: PCT/HU2012/000045
§ 371 (c)(1),
(2), (4) Date: Jan. 29, 2014

(87) PCT Pub. No.: WO2012/164324
PCT Pub. Date: Dec. 6, 2012

(65) Prior Publication Data
US 2014/0135503 A1    May 15, 2014

(30) Foreign Application Priority Data

Jun. 2, 2011  (HU) .................................... 1100291
Jun. 2, 2011  (HU) .................................... 1100292

(51) Int. Cl.
*C07C 69/74*      (2006.01)
*C07C 231/00*     (2006.01)
*C07D 209/48*     (2006.01)
*C07C 405/00*     (2006.01)
*C07D 207/46*     (2006.01)
*C07D 233/60*     (2006.01)
*C07D 307/935*    (2006.01)
*C07D 209/50*     (2006.01)

(52) U.S. Cl.
CPC ......... *C07C 405/0041* (2013.01); *C07C 405/00* (2013.01); *C07D 207/46* (2013.01); *C07D 209/48* (2013.01); *C07D 209/50* (2013.01); *C07D 233/60* (2013.01); *C07D 307/935* (2013.01); *C07B 2200/13* (2013.01); *C07C 2101/08* (2013.01)

(58) Field of Classification Search
USPC ............................ 560/121; 564/135; 548/475
See application file for complete search history.

(56) References Cited

U.S. PATENT DOCUMENTS

| 4,257,962 | A  | 3/1981 | Szabo et al. |
| 8,742,143 | B2* | 6/2014 | Henschke ............. C07C 67/333 |
| | | | 549/501 |
| 2005/0209337 | A1 | 9/2005 | Gutman et al. |
| 2009/0163596 | A1 | 6/2009 | Gutman et al. |
| 2009/0259058 | A1 | 10/2009 | Henschke et al. |

(Continued)

FOREIGN PATENT DOCUMENTS

| EP | 0660716 A1 | 7/1995 |
| EP | 2495235 A1 | 9/2012 |
| HU | 175889 | 3/1981 |

(Continued)

OTHER PUBLICATIONS

Akamatsu et al., "Synthesis and biodistribution study of liver-specific prostaglandin E, polymeric conjugate," International Journal of Pharmaceutics 155, 1997, pp. 65-74.

(Continued)

*Primary Examiner* — Nyeemah A Grazier
(74) *Attorney, Agent, or Firm* — Birch, Stewart, Kolasch & Birch, LLP

(57) ABSTRACT

The subject of the invention is process for the preparation of the prostaglandin amides of the general formula I, —where in the formula the bonds marked with dotted lines may be single or double bonds, in the case of double bounds at positions 5,6 and 13,14 they may be in cis or in trans orientation, Q stands for a hydroxyl-group and Z stands for a hydroxyl- or oxo-group, $R^1$ and $R^2$ independently represent hydrogen atom or a straight or branched $C_{1-10}$ alkyl- or aralkyl-group, optionally substituted with $—ONO_2$ group, or an aralkyl- or aryl-group, which contains heteroatom, $R^3$ represents a straight or branched, saturated or unsaturated $C_{4-6}$ hydrocarbon group, or a $C_{4-10}$ alkylcycloalkyl- or cycloalkyl-group, or an optionally with alkyl group or halogen atom substituted phenyl-, $C_{7-10}$ alkylaryl- or hetaryl-group, Y represents $(CH_2)_n$ group or 0 atom or S atom, and where n=0-3.

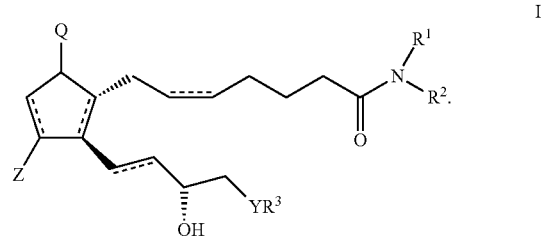

19 Claims, 11 Drawing Sheets

(56) References Cited

U.S. PATENT DOCUMENTS

2010/0105771 A1 4/2010 deLong et al.
2012/0270946 A1 10/2012 He et al.

FOREIGN PATENT DOCUMENTS

| HU | 178202 | 2/1983 |
|----|--------|--------|
| WO | WO 94/06433 A1 | 3/1994 |
| WO | WO 94/06750 A1 | 3/1994 |
| WO | WO 02/096868 A2 | 12/2002 |
| WO | WO 2005/058812 A2 | 6/2005 |
| WO | WO 2009/153206 A2 | 12/2009 |
| WO | WO 2011/046569 A1 | 4/2011 |
| WO | WO 2011/050638 A1 | 5/2011 |
| WO | WO 2011/055377 A1 | 5/2011 |
| WO | WO 2011/063276 A1 | 5/2011 |

OTHER PUBLICATIONS

Caira et al., "Crystalline Polymorphism of Organic Compounds," XP-001156954, 1998, pp. 163-208.
Gil et al. "Postaglandin E2-Bisphosphonate Conjugates: Potential Agents for Treatment of Osteoporosis," Bioorganic & Medicinal Chemistry 7, 1999, pp. 901-919.
Han et al. "Recent development of peptide coupling reagents in organic synthesis," Elsevier Tetrahedron 60, 2004, pp. 2447-2467.
International Search Report issued in PCT/HU2012/000045, mailed on Jul. 11, 2012.
PCT/ISA/237—Mailed on Jul. 11, 2012, issued in PCT/HU2012/000045.
Serkov et al., "Nitroanadamide, Nitroprostamides E2 and F2a, and Their Analogs," Chemistry of Natural Compounds, 2010 vol. 46, No. 5, pp. 696-700.

* cited by examiner

IR spectrum of the lactoltriol of example 1a.

IR spectrum of Bimatoprost acid of example 1/c1.

IR spectrum of form I. of example 14/a.

IR spectrum of form II. of example 10.)

DSC curve of form I. of example 14/a.

DSC curve of form II. of example 10.

X-ray diffraction curve of form I. of example 14/a.

X-ray diffraction curve of form II. of example 10.

X-ray diffraction curve of bimatoprost acid of example 1/c2.

DSC curve of bimatoprost acid of example 1/c2.)

PROCESSES FOR THE PREPARATION OF PROSTAGLANDIN AMIDES

The subject of the invention is a process for the preparation of prostaglandin amides of the general formula (I).

In the compounds of the general formula (I)

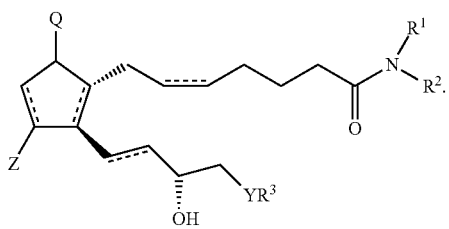

the meanings of the substituents are as follows:

the bonds marked with dotted lines may be single or double bonds, in the case of double bounds in positions 5,6 and 13,14 they may be in cis or in trans orientation, Q represents hydroxy-group and Z represents hydroxy- or oxo-group, $R^1$ and $R^2$ independently represent hydrogen atom or a straight or branched $C_{1-10}$ alkyl- or aralkyl-group, optionally substituted with $-ONO_2$ group, or an aralkyl- or aryl-group, which contains heteroatom, $R^3$ represents a straight or branched, saturated or unsaturated $C_{4-6}$ hydrocarbon group, or a $C_{4-10}$ alkylcycloalkyl- or cycloalkyl-group, or optionally with alkyl group or halogen atom substituted phenyl-, $C_{7-10}$ alkylaryl- or hetaryl-group, Y represents $(CH_2)$ group or O atom or S atom, and $n=0-3$.

To prepare the prostaglandin amide derivatives economically, the appropriately substituted prostan acid has to be activated.

According to the present state of the art, carboxylic acids may be activated by transformation into their
- mixed anhydrides
- activated esters or
- activated amides, and these compounds may then be further transformed into the desired prostaglandin amide derivatives by reaction with the appropriate amines.

Of the above possibilities, activation of the chemically very sensitive prostaglandin acids through ester formation is described for example in EP 0 660 716.

According to the process, the starting ester is formed with the help of alkyl halogenides and the ester is then reacted with the appropriate amine to give the amide function.

Disadvantage of the method is that the use of alkyl halogenides at the end of a synthesis—in the last step—is to avoid, since alkyl halogenides are proved to be genotoxic agents.

In addition, the resulting ester has to be treated with the appropriate amine at a high temperature for a long time and conversion rarely exceeds 50% (EP0660716 page 42, Example 12.). Considering the known temperature-sensitivity of prostaglandins, their treatment at high temperature unfavourably influences the impurity profile and the yield of the prostaglandin derivatives obtained in this way.

Preparation of the mixed anhydride and its reaction with the appropriately substituted amine is demonstrated in WO9153206.

Disadvantage of the method is that the active alkylating agents used for the preparation of the mixed anhydrides—halogenated formic acid esters, pivaloyl chlorides and others—are proved to be genotoxic compounds.

In the method described in WO2005058812 (page 23.) the starting carboxylic acid is directly transformed into the ethyl amide by use of the activating agent 1-(3-dimethylaminopropyl)-3-carbodiimide hydrochloride (EDC HCl) and ethylamine. During the amidation reaction the hydroxyl groups at positions 11 and 15 are protected with tetrahydropyran (THP) protecting group, which is then removed.

We have found that via the novel activated esters and novel activated amides according to the invention, the compounds of the general formula (I) can be prepared under mild reaction conditions in high yield and purity.

The compounds of the general formula (I) according to the invention can be prepared by reacting an acid of the general formula (II),

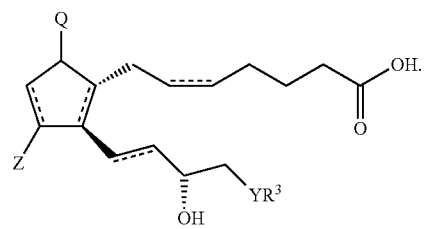

where in the formula the bonds marked with dotted lines may be single or double bonds, in the case of double bounds at positions 5,6 and 13,14 they may be in cis or in trans orientation, Q represents hydroxy-group and Z represents hydroxy- or oxo-group, $R^3$ represents a straight or branched, saturated or unsaturated $C_{4-6}$ hydrocarbon group, or a $C_{4-10}$ alkylcycloalkyl- or cycloalkyl-group, or optionally with alkyl group or halogen atom substituted phenyl-, $C_{7-10}$ alkylaryl- or hetaryl-group, Y represents $(CH_2)_n$ group or O atom or S atom, and $n=0-3$, i.) with a compound suitable for the introduction of group $R^4$, where $R^4$ represents a.)

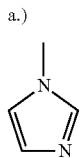

a group of formula a.), and reacting the amide of the general formula (III), thus obtained

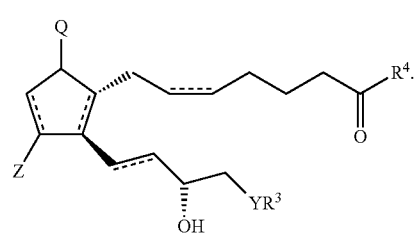

where the meanings of Q, Z, $R^3$, $R^4$, Y and n are as defined above, with an amine of the general formula (IV), $$NHR^1R^2 \quad\quad IV.$$

where the meanings of $R^1$ and $R^2$ are as defined above, or
ii.) with a compound suitable for the introduction of group $R^5$, where $R^5$ represents b.)

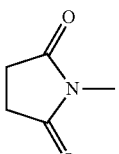

c.)

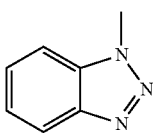

d.)

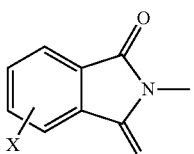

e.)

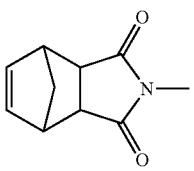

a group of formula b.), c.), d.) or e.), where X stands for halogen or hydrogen atom, and reacting the activated ester of the general formula (V), thus obtained

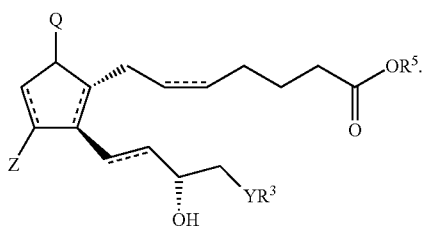

V where the meanings of Q, Z, $R^3$, $R^5$, Y and n are as defined above, with an amine of the general formula (IV), where the meanings of $R^1$ and $R^2$ are as defined above.

We have further found that the compounds of the general formula (I) according to the invention can also be prepared by reacting a compound of the general formula (II) with a compound of the general formula (IV)—where in the formulae the meanings of the substituents are as defined above—in the presence of 2-chloro-1,3-dimethylimidazolinium chloride and a base (method iii.).

The intermediates of the general formula (III) and (V) are novel compounds.

As for a compound suitable to introduce group $R^4$, preferably 1,1'-carbonyldiimidazole(DCI) or 1,1'-thiocarbonyldiimidazole, to introduce group $R^5$, in a given case in the presence of an activating agent, N-hydroxysuccinimide, N-hydroxyphthalimide, N-hydroxy-5-norben-endo-2,3-dicarboxamide, 1-hydroxybenzotriazole, (benzotriazol-1-yloxy)tris(dimethylamino)phosphonium hexafluorophosphate, N,N'-disuccinimidyl carbonate (DSC) or N,N'-disuccinimidyl oxalate, especially N,N'-disuccinimidyl carbonate may be applied.

As for activating agent N,N'-diisopropylcarbodiimide, N,N'-dicyclohexylcarbodiimide or 2-chloro-1,3-dimethylimidazolinium chloride, preferably N,N'-diisopropylcarbodiimide may be applied.

In the course of method i.) according to the invention, group $R^4$ can be introduced in an ether-type solvent or aromatic solvent or polar aprotic solvent or in their mixtures, using for example diisopropyl ether, tert-butyl methyl ether, 2-methyltetrahydofuran, toluene, anisole, dimethylformamide, dimethylsulfoxide, N-methylpyrrolidone, especially tetrahydrofuran. The resulting activated amide of the general formula (III) is reacted with the amine of the general formula (IV) after or without isolation.

The reaction temperature during the introduction of group $R^4$ is between 20-80° C., preferably 70° C., while the reaction of the compounds of formula (III) and (IV) is carried out between 20-80° C., preferably at room temperature.

In the course of method ii.) according to the invention, the introduction of group $R^5$ is carried out in an ether-type solvent or in an aromatic or polar aprotic solvent or in their mixtures, using for example diisopropyl ether, tert-butyl methyl ether, 2-methyltetrahydofuran, toluene, anisole, dimethylformamide, dimethylsulfoxide, N-methylpyrrolidone, especially tetrahydrofuran. The resulting activated ester of the general formula (V) is reacted with the amine of the general formula (IV) after or without isolation. The reaction temperature during the introduction of group $R^5$ is between 0-80° C., preferably at room temperature, while the reaction of the compounds of formula (V) and (IV) is carried out between 20-80° C., preferably at room temperature.

In the course of method iii.) according to the invention, the reaction is performed in an ether-type solvent or in an aromatic or polar aprotic solvent or in their mixtures, using for example diisopropyl ether, tert-butyl methyl ether, 2-methyltetrahydofuran, toluene, anisole, dimethylformamide, dimethylsulfoxide, N-methylpyrrolidone or tetrahydrofuran. As for base, the usually applied bases, like pyridine, N-methylmorpholine, diisopropylethylamine, 1,5-diazabicyclo[4,3,0]non-5-ene, 1,8-diazabicyclo[5,4,0]undec-7-ene or triethylamine may be employed.

The reaction is carried out at a temperature between 0-70° C., in such a way that to the solution of the compound of the general formula (II) in an organic solvent are added at 0-70° C., preferably at 30° C., the compound of the general formula (IV), the 2-chloro-1,3-dimethylimidazolinium chloride and 2 molar equivalent amount of the base. The mixture is first stirred at that temperature and then gradually heated until the starting material disappears. The reaction is followed by TLC.

Methods i, ii or iii may be carried out also under "one pot" conditions.

As for the amine of the general formula (IV) the amine appropriate for the final compound, in the case of bimatoprost ethylamine may be used.

For the preparation of the compounds of the general formula (IA)

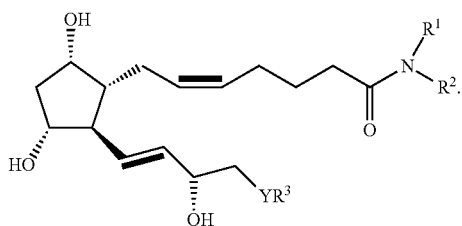

IA where in the formula the meanings of $R^1$, $R^2$, $R^3$, Y and n are as defined above, the compounds of the general formula (IIA) according to the invention are used as starting materials.

The compounds of the general formula (IIA)

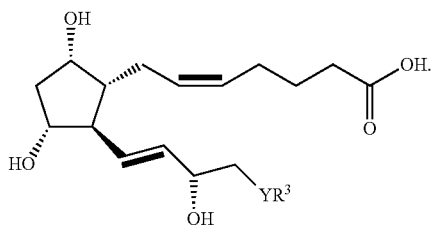

IIA where in the formula $R^3$ represents a straight or branched, saturated or unsaturated $C_{4-6}$ hydrocarbon group, or a $C_{4-10}$ alkylcycloalkyl- or cycloalkyl-group, or optionally with alkyl group or halogen atom substituted phenyl-, $C_{7-10}$ alkylaryl- or hetaryl-group, Y represents $(CH_2)_n$ group or O atom or S atom, and n=0-3, may be prepared according to the invention by reducing the lactondiol of the general formula (XII),

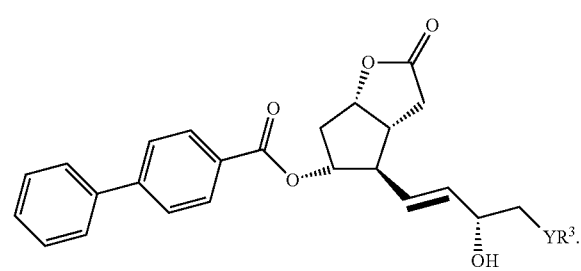

XII where in the meanings of $R^3$, Y and n are defined above, to the lactoltriol of the general formula (XIII),

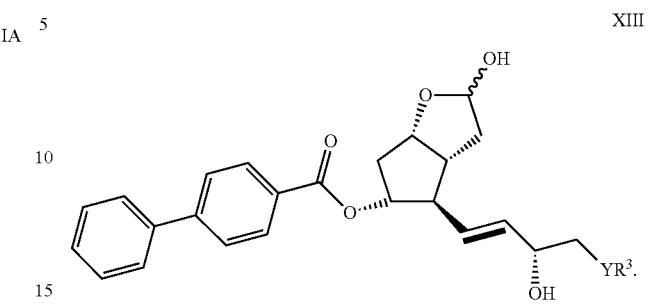

XIII where the meanings of $R^3$, Y and n are defined above, the protecting group of the compound of formula (XIII) is then removed, and the compound of the general formula (XIV), thus obtained,

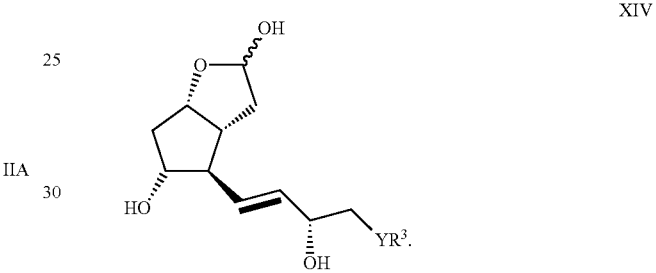

XIV where the meanings of $R^3$, Y and n are defined above, is transformed by Wittig reaction into the compound of the general formula (IIA).

Reduction of the compounds of the general formula (XII) may be carried out by known methods, for example with diisobutylaluminium hydride in tetrahydrofuran medium. The protecting group can be removed by known methods in acidic or alkaline medium, preferably in alkaline medium.

The lactoltriol derivatives of the general formula (XIII),

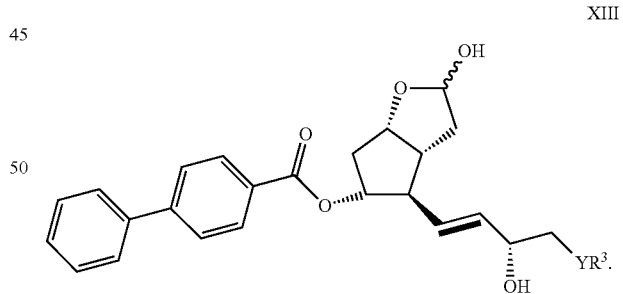

XIII where $R^3$ represents a straight or branched, saturated or unsaturated $C_{4-6}$ hydrocarbon group, or a $C_{4-10}$ alkylcycloalkyl- or cycloalkyl-group, or optionally with alkyl group or halogen atom substituted phenyl-, $C_{7-10}$ alkylaryl- or hetaryl-group, Y represents $(CH_2)_n$ group or O atom or S atom, and n=0-3, are novel compounds.

According to a further embodiment of the invention, the special compound of the general formula IIA, where $R^3$ stands for a phenyl group and Y stands for a —$(CH_2)$-group, compound of the formula (IIB) can be prepared also in crystalline form.

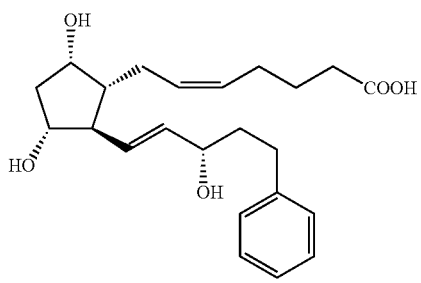

(IIB)

The crystalline form of the compound of the formula (IIB) is new.

The compound of the formula (IIB) can be prepared in crystalline form, in such a way that to a mixture containing the compound of the formula (IIB) a mixture of ester type and ether type solvents is added.

According to the process dimethyl ether, diethyl ether, diisopropyl ether, preferably diethyl-ether and diisopropyl ether are used as ether-type solvents, and ethyl-acetate, methyl-acetate, isopropyl-acetate, preferably isopropyl-acetate as ester-type solvents.

The crystallisation is performed between (−)30° C. and 30° C., preferably between 0-25° C.

The suspension of crystals, thus obtained is stirred 1-24 hours, preferably 8 hours, then filtered and washed with ether type solvent, preferably with diisopropyl ether.

The filtered crystals are dried under vacuum between 25-50° C., preferably at 35-40° C.

The compounds of the general formulae (II) and (XII) may be prepared by known methods, for example as described in U.S. Pat. No. 5,359,095, WO 93/00329.

The advantage of the method according to the invention is that the desired bimatoprost final product—if desired—may be synthesized through a crystalline bimatoprost acid. Further advantage of the method according to the invention is that the desired final product is synthesized through a novel intermediate, a crystalline, activated ester or amide, which—if desired—can be isolated and—if desired—can be purified by crystallisation or chromatography. Due to the applied carboxylic acid activating agents (e.g. DSC, DCI), the protection of the secondary hydroxyl groups in positions 9, 11 and 15 is not necessary, parallel reactions, for example dimer formation was not observed, either in the case of the activated ester or activated amide, or under the conditions of the final amide formation, and the activated carboxylic acid derivatives according to the invention were easily isolated with high yield and purity.

Surprisingly it was found that the crystalline activated carboxylic acid derivatives of the invention can be easily purified by crystallisation processes for eliminating the impurities and can also be transformed into the desired amide final product simply, under mild reaction conditions and in high yield.

It is well known that in case of an active pharmaceutical ingredient (API) the level of the impurities is a key issue, in case of bimatoprost the amount of every unknown impurity must be reduced under 0.1%. According to the process of the invention—to keep this very strict limitation—the crystallisation of bimatoprost acid and the crystallisation of the active carboxylic acid derivatives were used instead of the expensive preparative HPLC resolution described in WO09153206.

Further embodiment of our invention is a process for the preparation of a high melting crystal form II of bimatoprost of the formula (IB).

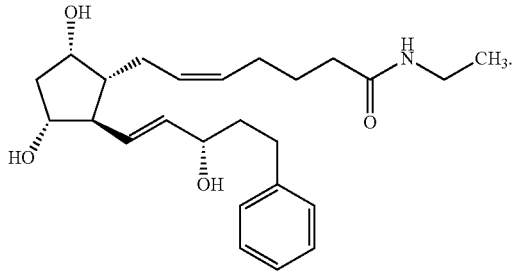

IB

By the process according to the invention a chemically and thermodynamically stable and from other crystal forms free, high melting crystal form II. of bimatoprost can be prepared.

The following patent applications deal with the crystallisation of bimatoprost product: US 2005/0209337 A1, WO 2009/153206 A2, US 2009/0163596 A1.

In Example 30 of US 2005/0209337 A1, the high melting point crystal form of bimatoprost (DSC peak read value 79° C.) (further on: crystal form II.) is characterized by its X-ray diffraction, by its IR spectrum in KBr pellet and by its DSC and TGA curves.

WO 2009/153206 describes the purification of bimatoprost product by preparative HPLC, followed by crystallisation. Crystallisation is carried out from acetonitrile solvent or from acetonitrile as dissolutiori and TBME (tert-butyl methyl ether) as precipitating solvent. According to the description, by that method the high melting point crystal form of bimatoprost (DSC peak read value 79° C.) can be prepared. By reproducing the method we did not succeed to obtain the high melting point crystal form of bimatoprost.

US 2009/0163596 discloses crystal form I. of bimatoprost and its preparation. Crystal form I. of bimatoprost is characterized by its melting point (62-64° C.), by DSC, X-ray diffraction and IR investigation. It describes in details the crystallisation process, such as the dissolution process (in an organic solvent or in the mixture of an organic dissolution—and precipitation—solvent at a temperature near the boiling point), the cooling process, the separation of the precipitated crystals from the mother liquor and the drying process (in vacuum at low temperature). The high melting point crystal form (DSC peak read value 79° C.) of bimatoprost cannot be prepared by the methods described in US 2009/0163596.

By the process of the invention the chemically and thermodynamically stable, high melting point crystal form II. of bimatoprost (=high melting point crystal form (DSC peak read value 79° C.)) can be prepared which is free of crystal form I. Form II. is characterized by its melting point (72-78° C.), by DSC investigation and by IR and X-ray powder diffraction studies.

The essence of the process is, that from a bimatoprost-containing reaction mixture after work-up and evaporation, or from any crystalline or non-crystalline form of bimatoprost or from their mixtures of any ratio, through crystallisation from a protic or ether-type solvent the thermodynamically stabile, pure form II. is prepared. The crystallisation process is the following: to the oily or crystalline crude bimatoprost calculated amount of the solvent is added, then it is dried and periodically exposed to mechanical effect.

In accordance with the above, our invention relates to a process for the preparation of form II. of bimatoprost of formula (IB), characterized in that to a bimatoprost-containing reaction mixture after work-up and evaporation, or to any crystalline or non-crystalline form of bimatoprost or to their mixtures of any ratio, calculated amount of an ether-type or protic solvent is added, if desired the resulting mixture is exposed to mechanical effect, then it is dried and homogenized.

The melting point of crystal form II. obtained in the above process is between 72-78° C., the endothermic peak, based on DSC investigation, is between 73-79° C. and the melting heat is higher than 75 J/g.

BRIEF DESCRIPTION OF THE DRAWINGS

FIG. 1 shows the IR spectrum of the lactoltriol of example 1a.

In the process according to the invention we use calculated amount, favourably 20-60 mass %, preferably 35 mass % amount of protic solvent, especially alcohols like methanol, ethanol and/or water. Preferably water is used as protic solvent.

As mechanical effect we apply stirring or scratching, or both. The added solvent is removed by drying. Drying is performed at a temperature between (−) 60° C. and 70° C., especially at 35° C., in vacuum.

As ether-type solvent we apply calculated amount, preferably 2000-8000 mass % amount of dimethyl ether, diethyl ether, diisopropyl ether, preferably diethyl ether. The added solvent is removed by drying. Drying is performed at low temperature, preferably between 0-(−)50° C. by passing through nitrogen gas.

Identification of the products was carried out with the help of the following analytical instruments:

NMR spectra were recorded by Bruker-Avance III-500 MHz instrument, DSC curves by Mettler-Toledo DSC 1/700 instrument, IR spectra by Perkin-Elmer Spektrum 400 FT-IR spectrophotometer, MS spectra by Shimadzu LC-MS-IT-TOF instrument. Melting points were determined by Büchi Melting Point B-545 apparatus.

Further details of the invention are described in the examples, without to limit the invention to the examples.

EXAMPLES

1. Preparation of the Starting Material a.) preparation of the [1,1'-Biphenyl]-4-carboxylic acid ((3aR,4R,5R,6aS)-hexahydro-4-[(1E,3S)-3-hydroxy-5-phenyl-1-penten-1-yl]-2-hydroxy-2H-cyclopenta[b]furan-5-yl) ester (PPB-lactoltriol)

The lacton group of 55 g of [1,1'-Biphenyl]-4-carboxylic acid ((3aR,4R,5R,6aS)-hexahydro-4-[(1E,3S)-3-hydroxy-5-phenyl-1-penten-1-yl]-2-oxo-2H-cyclopenta[b]furan-5-yl) ester (PPB-lactondiol)

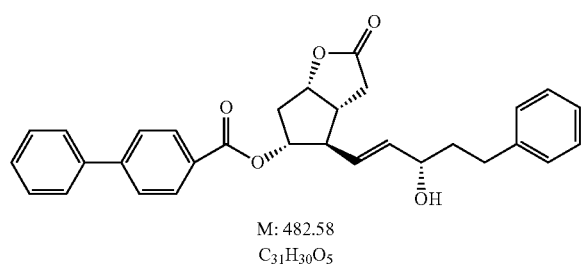 [SMILES: O=C1C[C@@H]2[C@@H](/C=C/[C@@H](O)CCc3ccccc3)[C@H](OC(=O)c3ccc(-c4ccccc4)cc3)C[C@@H]2O1]

M: 482.58
C$_{31}$H$_{30}$O$_5$ is reduced in 1000 ml of tetrahydrofuran (THF) solvent at (−)65-(−)85° C. with the hexane solution of 422 ml diisobutyl aluminium hydride (DIBAL-H). The reaction mixture is destroyed with NaHSO$_4$ solution, the aqueous phase is extracted with ethyl acetate, the organic phase is washed with NaHCO$_3$ solution and the solvent is removed at 40-50° C. The crude material is evaporated to obtain 46.2 g oil.

Structural formula of the obtained PPB-lactoltriol:

M: 484.60
C$_{31}$H$_{32}$O$_5$

From the crude oil after crystallization in tert-butyl methyl ether (TBME): hexane mixture, 41.6 g white crystals are obtained.

Melting point: 91.1-91.7° C.

Figure 1:
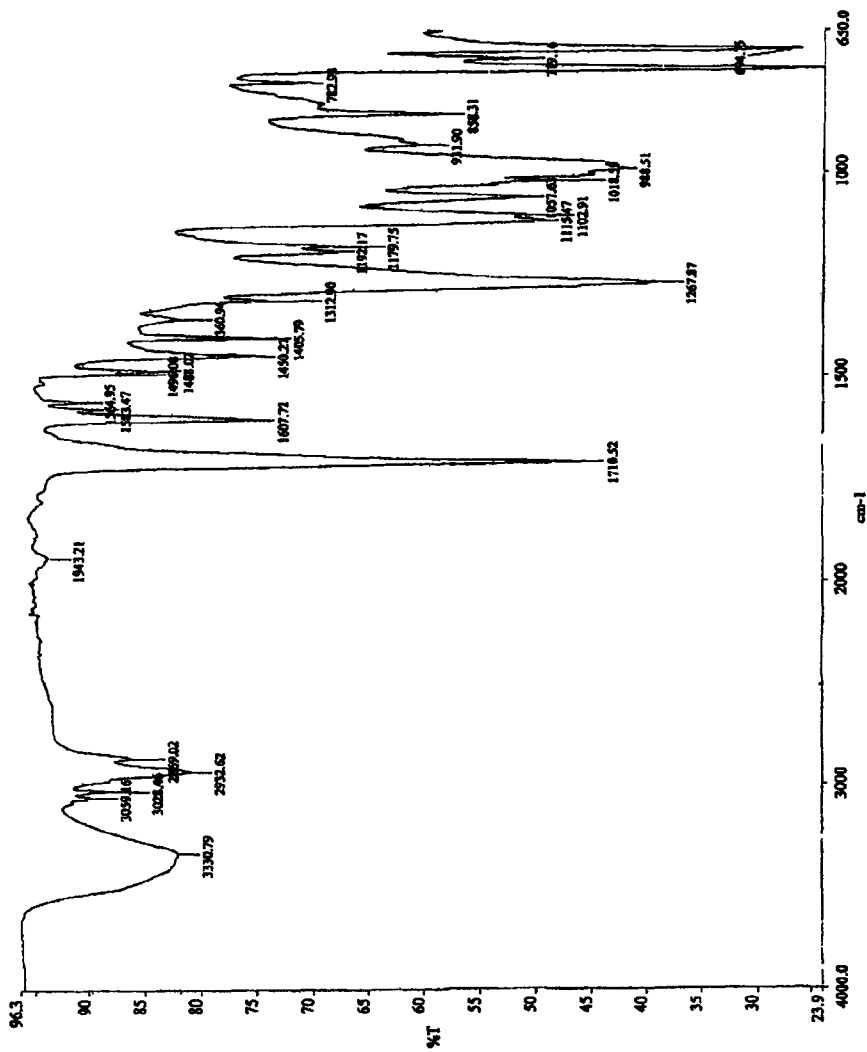

IR spectrum of the lactoltriol of example 1a. is shown FIG. 1. $^{13}$C and $^1$H NMR data:

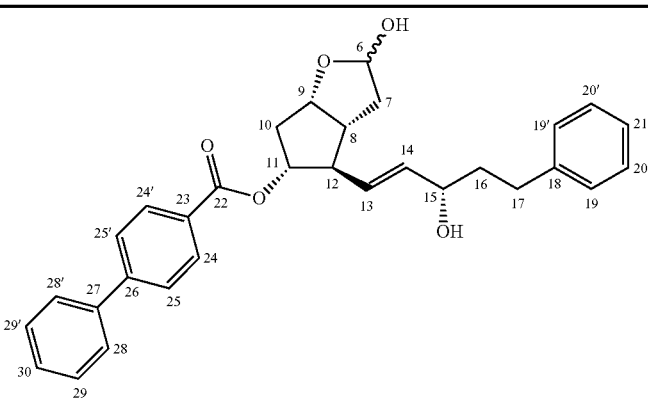

| Position | $^{13}C$ (ppm) | $^{1}H$ (ppm) | Number of the protons | Multiplicity | Coupling (Hz) |
|---|---|---|---|---|---|
| 6; OH | 99.72; 100.64 | 5.57* (20H); 5.49 OH: 6.05; 6.28 | 1 1 | m d | $J_{6,OH}$ = 4.65; 3.6 |
| 7 | 38.14; 38.44 | 2.57* (32H); 1.77 (39H) 1.78* (39H) | 1; 1 | m; m | 2.3-2.9; 7.0; $J_{7\alpha,7\beta}$ = 14.0 |
| 8 | 46.26; 45.69 | 2.57* (32H); 2.43 | 1 | m | —; $J_{8,9}$ = 8.85-9.1 |
| 9 | 80.19; 80.92 | 4.60; 4.50 | 1 | m | $J_{8,9}$ = 9.1; 2.7-3.3; 7.3-7.4; $J_{9,10}$ = 5.25 |
| 10 | 40.12**; 40.37** | 1.98; 1.93; 2.69; | 1; 1 | m; m | $J_{9,10}$ = 5.5; $J_{10\alpha,10\beta}$ = 13.6-13.65 |
| 11; OR | 80.54; 79.03 | 5.12; 5.05 | 1 | m | 7.1-7.3 7.4-7.55; 9.8 |
| 12 | 54.12; 53.22 | 2.55*(33H); 3.11 | 1 | m | —; 9.85-10.1; 7.55 |
| 13 | 129.38; 129.62 | 5.59* (19-20H); 5.59* (19-20H) | 1 | m | 6.3; $J_{13,14}$ = 15.3 |
| 14 | 136.66; 136.69 | 5.65* (17-18H); 5.65* (17-18H) | 1 | m | $J_{14,15}$ = 5.15; $J_{13,14}$ = 15.45 |
| 15; OH | 70.47; 70.39 | 3.98* (28H); 3.98* (28H) OH: 4.80* (24H); 4.79* (25H) | 1 1 | m d | $J_{14,15}$ = 5.2-5.5 $J_{15,OH}$ = 4.7; 4.8 |
| 16 | 40.09** | 1.71-1.61*(40H) | 1; 1 | m; m | |
| 17 | 31.86; 31.80 | 2.57* (32H); 2.55* (33H) | 2 | m | |
| 18 | 143.14 | — | — | — | — |
| 19, 19' | 129.06 | 7.10; 7.06 | 1 | d | $J_{19,20}$ = 7.3; 7.2 |
| 20, 20' | 129.09 | 7.23* (9H); 7.20* (10H) | 1 | t | $J_{19,20}$ = $J_{20,21}$ = 7.4; 7.5 |
| 21 | 126.41; 126.37 | 7.14* (11H); 7.13* (12H) | 1 | t | $J_{20,21}$ = 7.3-7.45 |
| 22 | 166.07; 166.16 | — | — | — | — |
| 23 | 129.52; 129.48 | — | — | — | — |
| 24, 24' | 130.71 | 8.04* (2H); 8.06* (1H) | 1 | d | $J_{24,25}$ = 8.3; 8.4 |
| 25, 25' | 127.86 | 7.83* (3H); 7.81* (4H) | 1 | d | $J_{24,25}$ = 8.5; 8.4 |
| 26 | 145.64 | — | — | — | — |
| 27 | 139.77 | — | — | — | — |
| 28, 28' | 127.90 | 7.75* (5H); 7.73* (6H) | 1 | d | $J_{28,29}$ = 7.6; 7.95 |
| 29, 29' | 130.01 | 7.55 | 1 | t | $J_{28,29}$ = $J_{29,30}$ = 7.4-7.8 |
| 30 | 129.33 | 7.47 | 1 | t | $J_{29,30}$ = 7.3-7.35 |

*Overlapping $^{1}H$ NMR signals (The number in brackets signifies the position number of the signal group in the PMR spectrum, direction: towards decreasing shifts)
**$^{13}C$ NMR signals overlapping with the multiplett of the DMSO solvent.

b.) Preparation of the (3aR,4R,5R,6aS)-hexahydro-4-[(1E,3S)-3-hydroxy-5-phenyl-1-penten-1-yl]-2H-cyclopenta[b]furan-2,5-diol, (lactoltriol):

46.2 g of [1,1'-Biphenyl]-4-carboxylic acid ((3aR,4R,5R,6aS)-hexahydro-4-[(1E,3S)-3-hydroxy-5-phenyl-1-penten-1-yl]-2-hydroxy-2H-cyclopenta[b]furan-5-yl) ester (PPB-lactoltriol) oil is dissolved in 230 ml of methanol and after adding 6.6 g of $K_2CO_3$ it is desacylated at 35-45° C. The pH of the reaction mixture is adjusted to 7-8 at (−)5-0° C. with 0.5 M phosphoric acid solution. The precipitated crystals are filtered off and washed with methanol:water mixture. The mother liquor is evaporated, extracted with ethyl acetate, the organic phase is dried over $Na_2SO_4$, the drying material is filtered off and the product is crystallized by the addition of hexane. 26 g of white crystalline material is obtained.

Structural Formula of the Product:

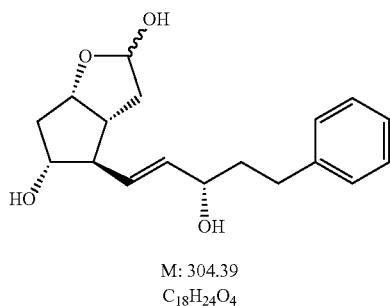

M: 304.39
$C_{18}H_{24}O_4$

Melting point: 98-103° C.

$^{13}$C and $^1$H NMR data:

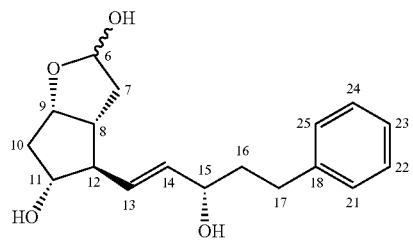

| Position | $^{13}$C (ppm) | $^1$H (ppm) | Number of the protons | Multiplicity | Coupling (Hz) |
|---|---|---|---|---|---|
| 6; OH | 99.65; 100.48 | 5.46* (8H); 5.40 | 1 | m | $J_{6,OH}$ = 4.65; 3.8 |
|  |  | OH: 5.92; 6.13 | 1 | d |  |
| 7 | 39.94; 38.77 | 1.81* (26H) | 1; 1 | m; m |  |
|  |  | 1.97* (25H); 1.66* (27H) |  |  |  |
| 8 | 45.63; 45.81 | 2.29* (22H); 2.22* (24H) | 1 | m |  |
| 9 | 79.20; 80.97 | 4.38; 4.32 | 1 | m | $J_{9,10a}$ = 6.9; 7.3-7.55 |
| 10 | 41.53; 43.795 | 2.27* (23H); 1.48 | 1; 1 | m; m | $J_{9,10a}$ = 6.4-6.8; 7.1-7.4 |
|  |  | 2.30* (22H); 1.76* (27H) |  |  |  |
| 11; OH | 77.62; 77.06 | 3.70; 3.61 | 1 | m | $J_{11,OH}$ = 5.95; 5.85 |
|  |  | OH: 4.75; 4.80 |  |  |  |
| 12 | 56.80; 55.86 | 1.97* (25H); 2.53* (21H) | 1 | m |  |
| 13 | 131.46; 132.11 | 5.54* (6H); 5.54* (6H) | 1 | m | $J_{13,14}$ = 15.3 |
| 14 | 135.39; 135.16 | 5.49* (7H); 5.49* (7H) | 1 | m | $J_{13,14}$ = 16 |
| 15; OH | 71.14; 71.22 | 3.94* (16H); 3.94* (16H) | 1 | m | $J_{15,OH}$ = 4.75; 4.35 |
|  |  | OH: 4.72* (12H); 4.71* (13H) | 1 | d |  |
| 16 | 40.26 | 1.74* (27H); 1.66* (27H) | 1; 1 | m; m |  |
| 17 | 32.24; 32.27 | 2.63* (20H); 2.63* (20H) | 1; 1 | m |  |
| 18 | 143.23 | — | — | — | — |
| 21* | 129.20 | 7.22* (2H) | 1 | d | $J_{21,22}$ = 7.3 |
| 22* | 129.18 | 7.30 | 1 | t | $J_{21,22}$ = $J_{22,23}$ = 7.4-7.6 |
| 23* | 126.48 | 7.19* (3H) | 1 | t | $J_{22,23}$ = $J_{23,24}$ = 7.25 |
| 24* | 129.18 | 7.30 | 1 | t | $J_{23,24}$ = $J_{24,25}$ = 7.4-7.6 |
| 25* | 129.20 | 7.22* (2H) | 1 | d | $J_{24,25}$ = 7.3 |

*Overlapping $^1$H NMR signals. (The number in brackets signifies the position number of the signal group in the PMR spectrum, direction: towards decreasing shifts).

c.) Preparation of the 7-[(1R,2R,3R,5S)-3,5-dihydroxy-2-[(1E,3S)-3-hydroxy-5-phenyl-1-penten-1-yl]-cyclopentyl]-5-heptenic acid, (5Z)-(bimatoprost acid):

c1.) 108 g of 4-carboxybutylphosphonium bromide (KBFBr) is dissolved in 800 ml of THF and the solution is cooled to 0-(−5)° C. To this solution first 91 g of potassium tert-butylate (KOtBu), and then after stirring and cooling to (−10)-(−15)° C., the solution of 25 g of lactoltriol in THF are added. When the expected conversion is reached the reaction mixture is destroyed with water, then EtOAc is added. The aqueous phase is washed with EtOAc. The aqueous layer is acidified with NaHSO$_4$ solution to pH=2 and extracted with EtOAc. The united organic phase is washed with 15% NaCl solution, dried over Na$_2$SO$_4$, filtered and evaporated. The residue is crystallized from the mixture of ethyl, acetate and diisopropyl ether. The crystals are filtered off and washed, the filtrate solution is evaporated. The resulting yellow oil is purified by chromatography on silica gel using diisopropyl ether—acetone eluent.

25.5 g oil is obtained.

Figure 2:
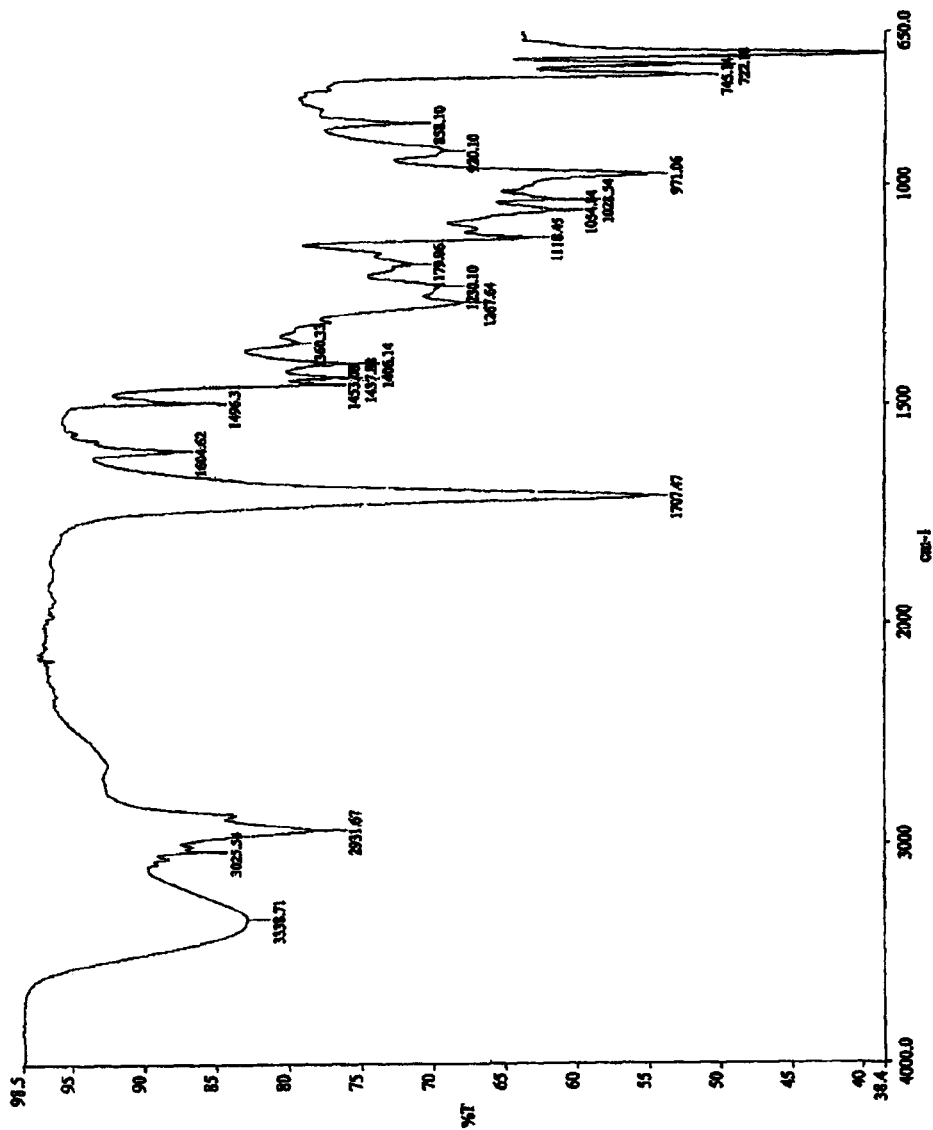
FIG. 2 shows the IR spectrum of the obtained Bimatoprost acid.

IR spectrum of the obtained Bimatoprost acid is shown in FIG. 2.

c2.) The product obtained in example 1/c1.) is dissolved in 60 ml of isopropyl-acetate and under stirring 40 ml of diethyl-ether is added to it. Small amount of bimatoprost acid seeding crystal is added to the reaction mixture. Under stirring gradually cooled to 0° C. about 60 ml of diisopropyl-ether is added to it. The suspension is stirred at this temperature for a night thereafter it is filtered and washed with diisopropyl-ether and dried under vacuum. 20.4 g crystalline bimatoprost acid is obtained.

Figure 9:
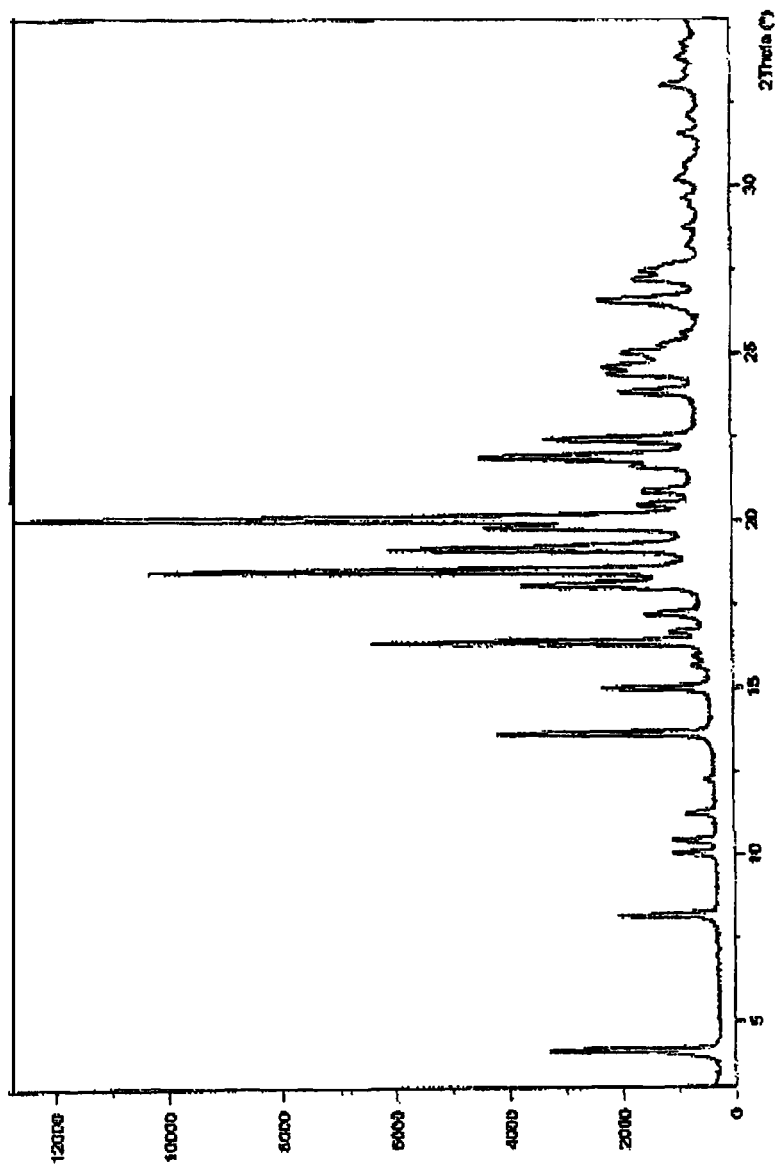
FIG. 9 shows the X-ray powder diffraction curve of the obtained Bimatoprost acid.
Figure 10:
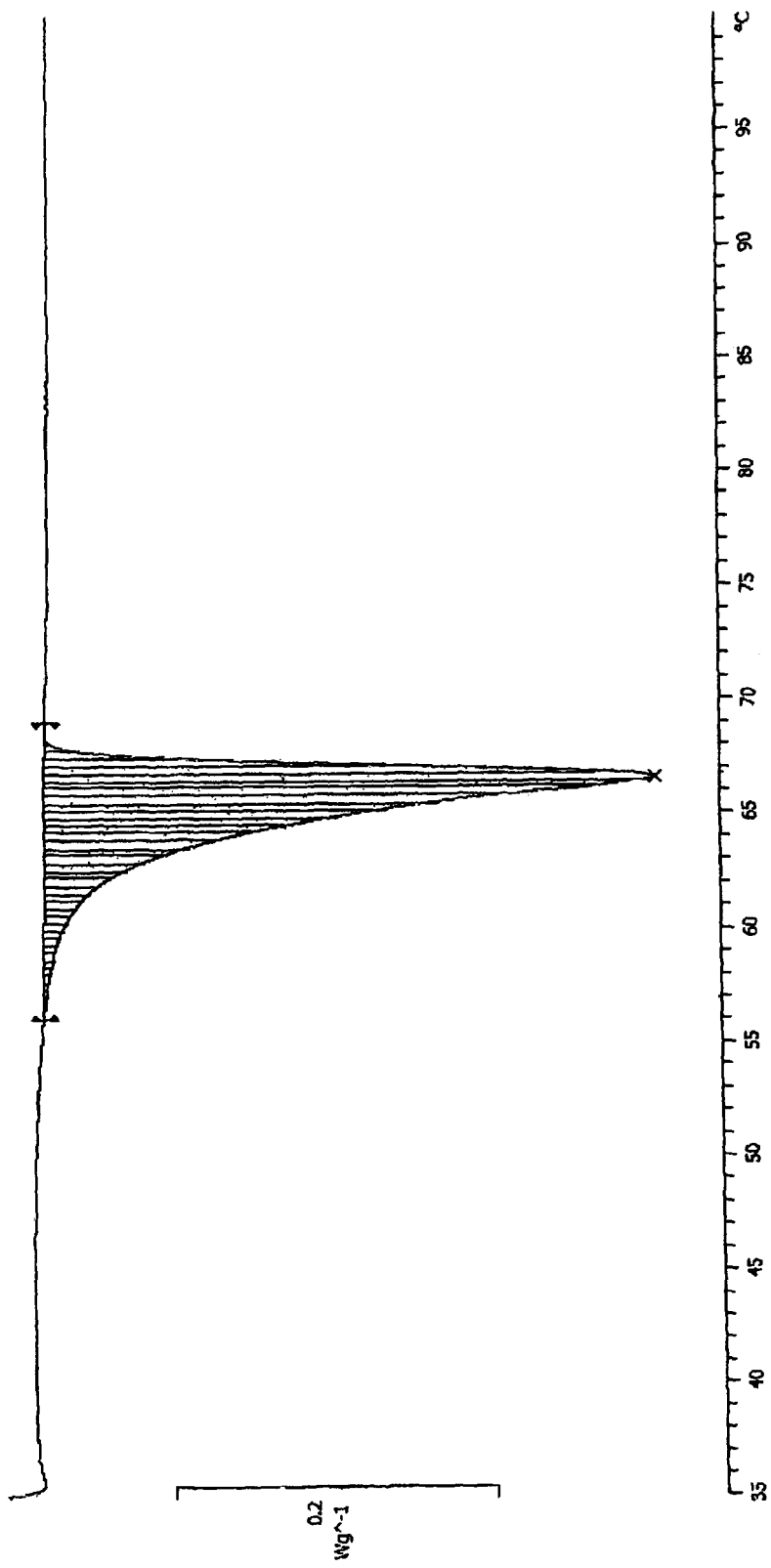
FIG. 10 shows the DSC curve of the obtained Bimatoprost acid.

DSC curve of the obtained Bimatoprost acid is shown in FIG. 10 and X-ray powder diffraction curve in FIG. 9.

Structural formula of the product:

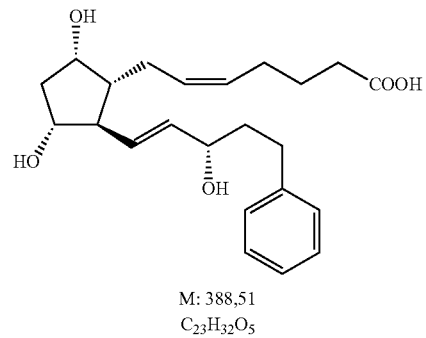 [SMILES: O=C(O)CCC/C=C\C[C@@H]1[C@@H](/C=C/[C@@H](O)CCc2ccccc2)[C@H](O)C[C@@H]1O]

M: 388,51
$C_{23}H_{32}O_5$

Melting point: 63.0-65.5° C.

$^{13}C$ and $^1H$ NMR data:

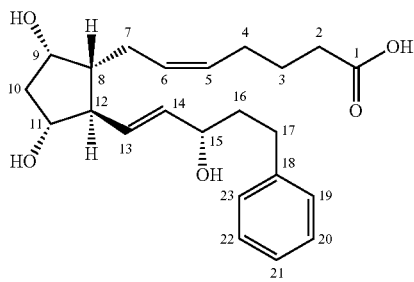 [SMILES: O=C(O)CCC/C=C\C[C@@H]1[C@@H](/C=C/[C@@H](O)CCc2ccccc2)[C@H](O)C[C@@H]1O]

| Position | $^{13}C$ (ppm) | $^1H$ (ppm) | Number of the protons | Multiplicity | Coupling (Hz) |
|---|---|---|---|---|---|
| 1; COOH | 175.30 | -; COOH: 12.02 | -; COOH: 1 | -; COOH: broad | |
| 2 | 34.10 | 2.23* (21H); 2.16* (22H) | 1; 1 | m; m | |
| 3 | 25.45 | 1.54* (26H) | 2 | m | |
| 4 | 27.09 | 2.01* (24H) | 2 | m | $J_{4,5} = 6.8$-$7.0$ |
| 5 | 129.53 | 5.29 | 1 | td | $J_{4,5} = 7.2$ $J_{5,6} = 10.8$ |
| 6 | 130.64 | 5.50* (7H) | 1 | td | $J_{6,7} = 7.8$ $J_{5,6} = 10.6$ |
| 7 | 25.74 | 2.15* (22H); 2.04* (24H) | 1; 1 | m; m | |
| 8 | 49.81 | 1.34 | 1 | m | $J_{8,9} = 5.75$ |
| 9; OH | 70.47 | 3.95* (13H); OH: 4.40 | 1 | m; broad | $J_{8,9} = 5.75$ |
| 10 | 44.89 | 2.24*(21H); 1.48* (26H) | 1; 1 | m; ddd | $J_{10\alpha,10\beta} = 14.1$; 5.65-5.85; 2.3-2.4 |
| 11; OH | 76.69 | 3.71; OH: 4.55 | 1; OH: 1 | m (ddd); broad | $J_{11,12} = 7.5$ |
| 12 | 55.22 | 2.19* (21H) | 1 | m | |
| 13 | 133.05 | 5.40* (7H) | 1 | dd | $J_{12,13} = 7.7$-$8.15$; $J_{13,14} = 15.45$ |
| 14 | 136.09 | 5.47* (7H) | 1 | dd | $J_{14,15} = 6.2$-$6.35$; $J_{13,14} = 15.4$ |
| 15; OH | 71.53 | 3.94* (13H); OH: 4.71 | 1; OH: 1 | m; broad | $J_{14,15} = 6.4$ |
| 16 | 40.45* | 1.75* (25H); 1.69* (25H) | 1; 1 | m; m | |
| 17 | 32.29 | 2.64 | 2 | m | |
| 18 | 143.24 | — | — | — | — |
| 19* | 129.15 | 7.21* (5H) | 1 | d | $J_{19,20} = 6.9$ |
| 20* | 129.20 | 7.30 | 1 | t | $J_{19,20} = J_{20,21} = 7.5$-$7.55$ |
| 21* | 126.51 | 7.19* (5H) | 1 | t | $J_{20,21} = J_{21,22} = 6.7$-$7.3$ |
| 22* | 129.20 | 7.30 | 1 | t | $J_{21,22} = J_{22,23} = 7.5$-$7.55$ |
| 23* | 129.15 | 7.21* (5H) | 1 | d | $J_{22,23} = 6.9$ |

*Partly or fully overlapping $^1H$ NMR signals. (The number in brackets signifies the position number of the signal group in the PMR spectrum, direction: towards decreasing shifts).

2. Preparation of 7-[3,5-Dihydroxy-2-(3-hydroxy-5-phenyl-pent-1-enyl)-cyclopentyl]-5-heptenoic acid (2,5-dioxo-pyrrolidin-1-yl) ester (activated ester)

27.5 g of bimatoprost acid of example 1/c2.) is dissolved in 270 ml of THF and to it are added at room temperature 13.7 g of N,N'-diisopropylcarbodiimide followed by 13.7 g of N-hydroxysuccinimide. The mixture is stirred at that temperature and then poured onto the mixture of 1N $NaHSO_4$ solution and tert-butyl methyl ether (TBME). The phases are separated. The organic phase is washed with 1N $NaHCO_3$ solution, the aqueous-alkaline phase is extracted with TBME. The united organic phase is dried over $Na_2SO_4$, filtered and evaporated. The residue is crystallized from hexane:acetone mixture to obtain 30.04 g white crystalline material.

Product:

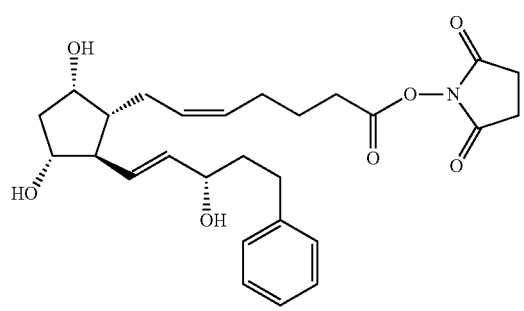

activated ester
$C_{27}H_{35}NO_7$
M = 485.58

Melting point: 93.5-103.4° C.

3.)

27.5 g of bimatoprost acid of example 1/c1.) is dissolved in 270 ml of THF and to this solution are added at room temperature 11.5 g of potassium carbonate and 19.6 g of N,N'-disuccinimidyl carbonate. The reaction mixture is under stirring gradually heated to 60° C. and then poured onto the mixture of 1N NaHSO$_4$ solution and tert-butyl methyl ether (TBME). The phases are separated, the organic phase is washed with 1N NaHCO$_3$ solution and the aqueous-alkaline phase is extracted with TBME. The united organic phase is dried over Na$_2$SO$_4$, filtered and evaporated. The residue is crystallized from hexane:acetone mixture to obtain 30.9 g white crystalline material.

Product:

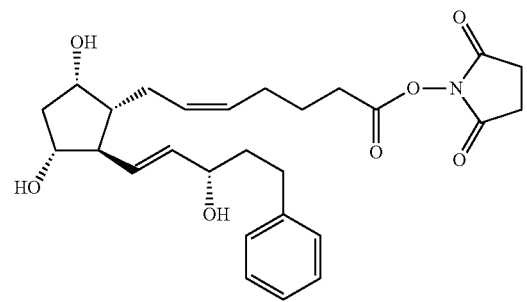

activated ester
$C_{27}H_{35}NO_7$
M = 485.58

Melting point: 93.5-103.4° C.
$^{13}C$ and $^1H$ NMR data:

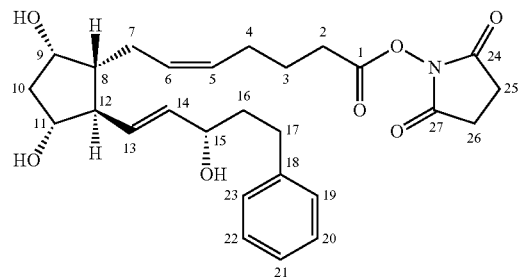 [SMILES: O=C(CCC/C=C\C[C@@H]1[C@@H](/C=C/[C@@H](O)CCc2ccccc2)[C@H](O)C[C@@H]1O)ON1C(=O)CCC1=O]

| Numbering | $^{13}C$ (ppm) | $^1H$ (ppm) | Number of $^1H$ | Multiplicity | Coupling constant (Hz) (+/−0.2 Hz) |
|---|---|---|---|---|---|
| 1 | 168.80 | — | — | — | |
| 2 | 29.70 | 2.55** | 2 | t | $J_{2,3}$ = 7.4 |
| 3 | 24.29 | 1.61*** | 2 | m (tt) | $J_{3,4}$ = 7.4 |
| 4 | 25.70 | 2.06 | 2 | m | $J_{4,5}$ = 7.2 |
| 5 | 127.87 | 5.28 | 1 | dt | $J_{5,6}$ = 10.7 |
| 6 | 130.27 | 5.48+ | 1 | dt (ddd) | $J_{6,7}$ = 7.4 |
| 7 | 24.83 | 7a: 2.14++ | 1 | m | |
|  |  | 7b: 2.00 | 1 | m | |
| 8 | 48.78 | 1.32 | 1 | m (dddd) | 10.4; 10.4; 5.1; 5.1 |
| 9 | 69.53 | 3.915+++ | 1 | m | |
| 9-OH |  | 4.35 | 1 | d | $J_{9,OH}$ = 5.0 |
| 10 | 43.94 | β: 2.20++ | 1 | m(ddd) | $J_{gem}$ = 14.1; 8.2; 5.9 |
|  |  | α: 1.44 | 1 | ddd | 5.6; 2.3 |
| 11 | 75.37 | 3.68 | 1 | m (dddd) | ~7.9; ~7.9; ~5.8; ~5.8 |
| 11-OH |  | 4.50 | 1 | d | $J_{11,OH}$ = 5.8 |
| 12 | 54.22 | 2.16++ | 1 | m | 7.8; 3.8 |
| 13 | 132.02 | 5.37 | 1 | dd | $J_{13,14}$ = 15.4; $J_{12,13}$ = 8.1 |
| 14 | 135.16 | 5.44+ | 1 | m (dd) | $J_{14,15}$ = 6.3 |
| 15 | 70.56 | 3.909+++ | 1 | m | |
| 15-OH |  | 4.65 | 1 | d | $J_{15,OH}$ = 4.7 |
| 16 | 39.49* | 1.71*** | 1 | m | |
|  |  | 1.65*** | 1 | m | |
| 17 | 31.35 | 2.60** | 2 | m | |
| 18 | 142.31 | — | — | — | |
| 19, 23 | 128.19/128.24 | 7.17# | 2 | d | $J_{19,20}$ = 7.4 |
| 20, 22 | 128.24/128.19 | 7.26 | 2 | t | $J_{20,21}$ = 7.4 |
| 21 | 125.55 | 7.15# | 1 | t | |
| 24, 27 | 170.18 | — | — | — | |
| 25, 26 | 25.42 | 2.80 | 4 | s | |

*Overlapped $^{13}C$ NMR by the DMSO signal.
, *, +, ++, +++, #Overlapped $^1H$ NMR signals.

4.) Preparation of 7-[3,5-Dihydroxy-2-(3-hydroxy-5-phenyl-pent-1-enyl)-cyclopentyl]-5-heptenoic acid 1,3-dioxo-1,3-dihydro-isoindol-2-yl ester (activated ester)

2 g of bimatoprost acid is dissolved in 20 ml of THF and to this solution are added at room temperature 1 g of N-hydroxyphtalimide and 1 ml of N,N'-diisopropylcarbodiimide. The reaction mixture is stirred for 2 hours and then poured onto they mixture of 1N $NaHSO_4$ solution and tert-butyl methyl ether (TBME). The phases are separated, the organic phase is washed with 1N $NaHCO_3$ solution and the aqueous-alkaline phase is extracted with TBME. The united organic phase is dried over $Na_2SO_4$, filtered and evaporated. The residue is crystallized from hexane:acetone mixture to obtain 1.5 g white crystalline material.

Product:

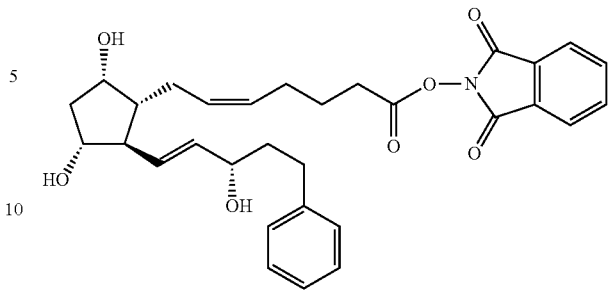

M: 533.63
$C_{31}H_{35}NO_7$

Melting point: 83.2-84.5° C.

$^{13}C$ and $^1H$ NMR data:

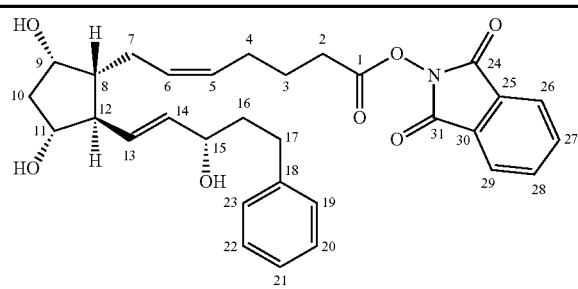

| Numbering | $^{13}C$ (ppm) | $^1H$ (ppm) | Number of $^1H$ | Multiplicity | Coupling constant (Hz) (+/−0.2 Hz) |
|---|---|---|---|---|---|
| 1 | 169.82 | — | — | — | |
| 2 | 29.63 | 2.64 | 2 | t | $J_{2,3} = 7.4$ |
| 3 | 24.29 | 1.65* | 2 | m (tt) | $J_{3,4} = 7.4$ |
| 4 | 25.71 | 2.09 | 2 | m | $J_{4,5} = 7.2$ |
| 5 | 127.84 | 5.30 | 1 | dt | $J_{5,6} = 10.5$ |
| 6 | 130.33 | 5.50 | 1 | dt (ddd) | $J_{6,7} = 7.5$ |
| 7 | 24.83 | a: 2.16** | 1 | m | $J_{gem} = 12.6$ |
|  |  | b: 2.01 | 1 | m (ddd) |  |
| 8 | 48.79 | 1.325 | 1 | m (dddd/tt) | 10.7, 10.0; 5.3; 4.7 |
| 9 | 69.52 | 3.92*** | 1 | m |  |
| 9-OH |  | 4.38 | 1 | d | $J_{9,OH} = 4.9$ |
| 10 | 43.95 | β: 2.205** | 1 | m(ddd) | $J_{gem} = 14.1$; $J_{10β} = 8.4$ and 6.0 |
|  |  | α: 1.44 | 1 | ddd | $J_{10α} = 5.6$ and 2.1 |
| 11 | 75.74 | 3.68 | 1 | m (dddd/tt) | ~7.8; ~7.8; ~6.0; ~6.0 |
| 11-OH |  | 4.52 | 1 | d | $J_{11,OH} = 5.8$ |
| 12 | 54.23 | 2.165** | 1 | m |  |
| 13 | 132.08 | 5.37 | 1 | dd | $J_{13,14} = 15.4$; $J_{12,13} = 8.3$ |
| 14 | 135.18 | 5.44 | 1 | m (dd) | $J_{14,15} = 6.4$ |
| 15 | 70.56 | 3.89*** | 1 | m |  |
| 15-OH |  | 4.66 | 1 | d | $J_{15,OH} = 4.6$ |
| 16 | 39.47$ | a: 1.69* | 1 | m |  |
|  |  | b: 1.64* | 1 | m |  |
| 17 | 31.34 | 2.58** | 2 | m (td) | 10.1 and 6.3 |
| 18 | 142.28 | — | — | — |  |
| 19, 23 | 128.16$/128.20 | 7.15+ | 2 | d | $J_{19,20} = 7.5$ |
| 20, 22 | 128.20/128.16$ | 7.24 | 2 | t | $J_{20,21} = 7.3$ |
| 21 | 125.52 | 7.13+ | 1 | t |  |
| 24, 31 | 161.81 | — | — | — |  |
| 25, 30 | ~128.1$ | — | — | — |  |
| 26, 29 | 123.97 | 7.97++ | 2 | m |  |
| 27, 30 | 135.51 | 7.94++ | 2 | m |  |

$Overlapped $^{13}C$ NMR by the DMSO signal.
$$Overlapped $^{13}C$ NMR signals.
*, , *, +, ++Overlapped $^1H$ NMR signals.

5.) Preparation of 7-[(1R,2R,3R,5S)-3,5-dihydroxy-2-[(1E,3S)-3-hydroxy-5-phenyl-1-pentenyl]-cyclopentyl]-N-ethyl-5-heptenamide, (5Z(−)bimatoprost) through the activated ester 27.5 g of bimatoprost acid is dissolved in 270 ml of THF and to the solution are added at room temperature 13.7 g N,N'-diisopropylcarbodiimide and then 13.7 g of N-hydroxysuccinimide. The mixture is stirred at room temperature. The resulting activated ester is not isolated.

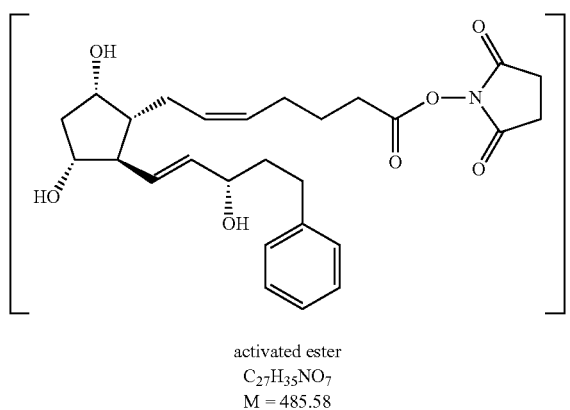

activated ester
$C_{27}H_{35}NO_7$
M = 485.58

After the completion of the ester formation 70 ml of 2M ethylamine in THF solution is added to the reaction mixture. The mixture is stirred until the expected conversion is reached, then it is poured onto the mixture of 1N $NaHSO_4$ solution and tert-butyl methyl ether (TBME). The phases are separated, the organic phase is washed with 1N $NaHCO_3$ solution and the aqueous-alkaline phase is extracted with TBME. The united organic phase is dried over $Na_2SO_4$, filtered and evaporated to obtain 25.4 g of oil.

Product:

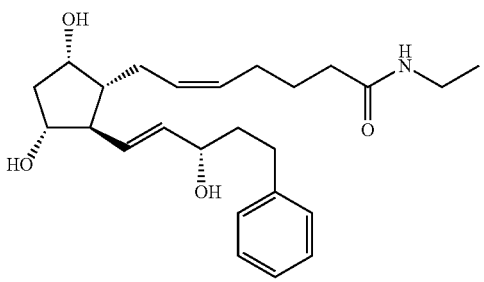

Bimatoprost
M: 415.58
$C_{25}H_{37}NO_4$ $^{13}C$ and $^1H$ NMR data:

| Position | $^{13}C$ (ppm) | $^1H$ (ppm) | Number of the protons | Multiplicity | Coupling (Hz) (+/−0.2 Hz) |
|---|---|---|---|---|---|
| 1 | 172.51 | — | — | — | |
| 2 | 35.88 | 2.02** | 2 | t | $J_{2,3}$ = 7.5 |
| 3 | 26.27 | 1.53*** | 2 | m (tt) | $J_{3,4}$ = 7.5 |
| 4 | 27.25 | 1.99** | 2 | m | $J_{4,5}$ = 7.2 |
| 5 | 129.78 | 5.30 | 1 | dt | $J_{5,6}$ = 10.5 |
| 6 | 130.38 | 5.48+ | 1 | Dt (ddd) | |
| 7 | 25.72 | 2.15++ | 1 | m | |
|  |  | 2.03** | 1 | m | |
| 8 | 49.78 | 1.35 | 1 | m (dddd) | 10.6; 10.6; 4.7; 4.7 |
| 9 | 70.45 | 3.95+++ | 1 | m | |
| 9-OH |  | 4.40 | 1 | d | $J_{9,OH}$ = 4.9 |
| 10 | 44.85 | β: 2.23++ | 1 | m | $J_{gem}$ = 14.2; |
|  |  | α: 1.48*** | 1 | ddd | 5.5; 2.2 |
| 11 | 76.67 | 3.71 | 1 | m (dddd) | ~7.5; ~7.5; ~7.5; 6.5 |
| 11-OH |  | 4.54 | 1 | d | $J_{9,OH}$ = 5.8 |
| 12 | 55.15 | 2.19++ | 1 | m | |
| 13 | 132.91 | 5.41 | 1 | dd | $J_{13,14}$ = 15.4; $J_{12,13}$ = 8.0 |
| 14 | 136.00 | 5.47+ | 1 | M (dd) | |
| 15 | 71.41 | 3.94+++ | 1 | m | |
| 15-OH |  | 4.71 | 1 | d | $J_{15,OH}$ = 4.6 |
| 16 | 40.36* | 1.74# | 1 | m | |
|  |  | 1.70# | 1 | m | |
| 17 | 32.25 | 2.61 | 1 | m | |
|  |  | 2.675 | 1 | m | |
| 18 | 143.21 | — | — | — | |
| 19, 23 | 129.13 | 7.21## | 2 | d | $J_{19,20}$ = 7.4 |
| 20, 22 | 129.15 | 7.30 | 2 | t | $J_{20,21}$ = 7.4 |
| 21 | 126.46 | 7.19### | 1 | t | |
| 24 (NH) |  | 7.72 | 1 | broad, t | $J_{24,25}$ = 5.5 |
| 25 | 34.13 | 3.07 | 2 | qd | $J_{25,26}$ = 7.2 |
| 26 | 15.70 | 1.02 | 3 | t | |

Figure 11A:
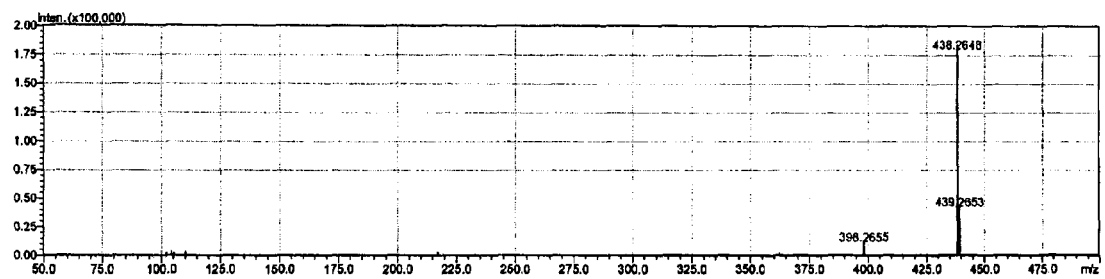
FIG. 11A shows the MS spectrum for positive ionization of Example 5.

The MS spectrum for positive ionization is shown in FIG. 11A.

Figure 11B:
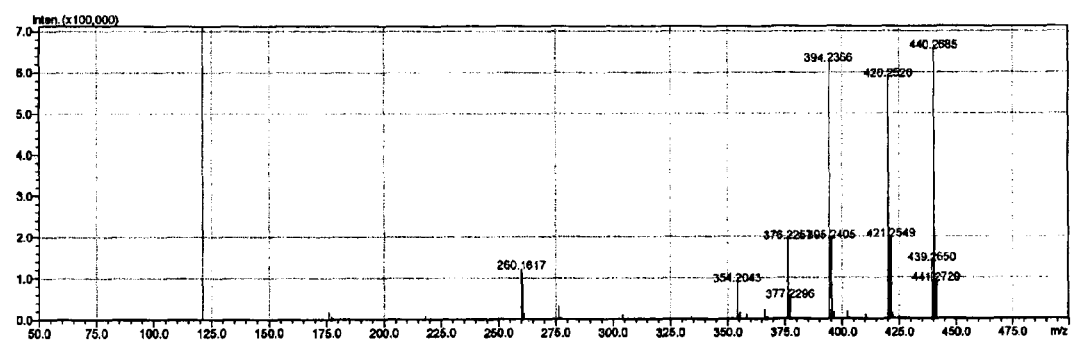
FIG. 11B shows the MSMS (precursor ion: 438.26) data of Example 5.

Expected formula:
$C_{25}H_{37}NO_4$
Measured exact mass: 438.2648 [M + Na]+
Expected exact mass: 438.2615 [M + Na]+    ΔM = 3.3 mDa and 7.53 ppm $C_{25}H_{35}NO_3$ (M − $H_2O$)
Measured exact mass: 398.2655 [M − $H_2O$ + H]+
Expected exact mass: 398.2690 [M − $H_2O$ + H]+    ΔM = −3.5 mDa and 8.79 ppm The MSMS (precursor ion: 438.26) data is shown in FIG. 11B.

Expected formula:

$C_{25}H_{35}NO_3$(M—$H_2O$)

Measured exact mass: 420.2520 [M − H2O + Na]+     ΔM = 1.1 mDa and 2.62 ppm
Expected exact mass: 420.2509 [M − H2O + Na]+
$C_{25}H_{32}NO_3$ (M − $H_2O$ − 5H)
Measured exact mass: 394.2366 [M − $H_2O$ − 5H]+     ΔM = −1.1 mDa and 2.79 ppm
Expected exact mass: 394.2377 [M − $H_2O$ − 5H]+
$C_{25}H_{30}NO_2$ (M − 2x$H_2O$ − 5H)
Measured exact mass: 376.2258 [M − 2x$H_2O$ − 5H]+     ΔM = −1.3 mDa and 3.46 ppm
Expected exact mass: 376.2271 [M − 2x$H_2O$ − 5H]+

6.) Preparation of Bimatoprost through the Activated Ester 27.5 g of bimatoprost acid is dissolved in 270 ml of THF and to this solution are added at room temperature 11.5 g of potassium carbonate and 19.6 g of N,N'-disuccinimidyl carbonate. The reaction mixture is gradually heated to 60° C. under stirring. The resulting activated ester is not isolated.

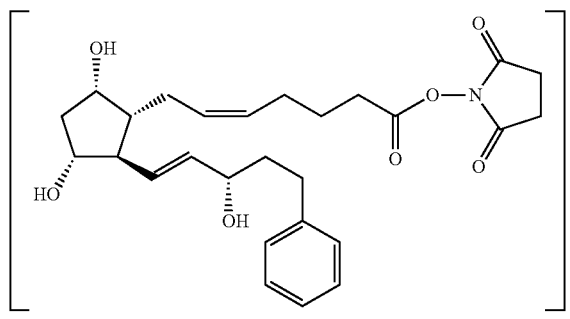

activated ester
$C_{27}H_{35}NO_7$
M = 485.58

After the formation of the activated ester, 70 ml of 2M ethylamine in THF solution is added to the reaction mixture. When the reaction is completed the mixture is poured onto the mixture of 1N $NaHSO_4$ solution and EtOAc. The organic phase is washed with 1N $NaHCO_3$ solution, the aqueous-alkaline phase is extracted with EtOAc. The united organic phase is washed with NaCl solution and dried over $Na_2SO_4$. The drying material is filtered off, the filtrate is evaporated to obtain 25.7 g of oil.

Product:

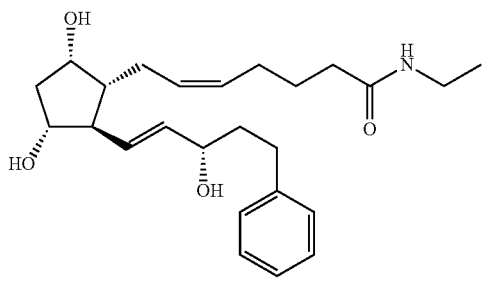

Bimatoprost
M: 415.58
$C_{25}H_{37}NO_4$

7.) Preparation of Bimatoprost through the Activated Amide 27.5 g bimatoprost acid is dissolved in 270 ml of pyridine and 13.7 g of 1,1'-carbonyldiimidazole is added to it. The mixture is stirred at 20-25° C. until the activated amide formation takes place. The resulting activated amide is not isolated.

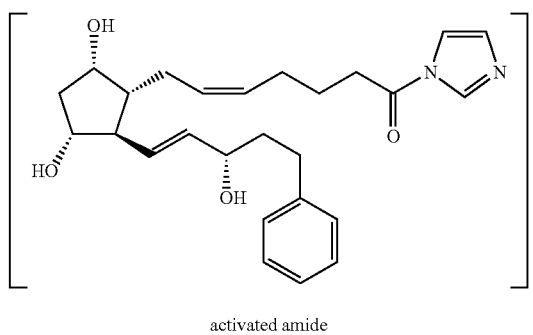

activated amide
$C_{26}H_{34}N_2O_4$
M = 438.57

70 ml of 2M ethylamine in THF solution is added to the reaction mixture at room temperature and the mixture is stirred until the expected conversion is reached. The mixture is then poured onto the mixture of 1N $NaHSO_4$ solution and tert-butyl methyl ether (TBME). The phases are separated, the organic phase is washed with 1N $NaHCO_3$ solution and the aqueous-alkaline phase is extracted with TBME. The united organic phase is dried over $Na_2SO_4$, filtered and the filtrate is evaporated to obtain 23.82 g of oil.

Product:

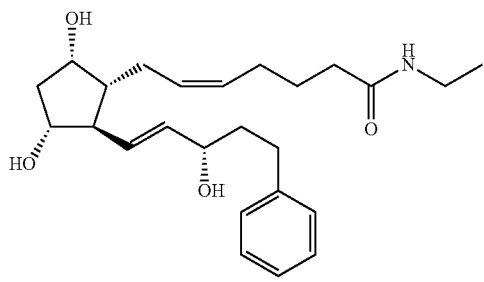

Bimatoprost
M: 415.58
$C_{25}H_{37}NO_4$

8.) Preparation of Bimatoprost from the Purified Activated Ester 30.9 g of the activated ester according to Example 3. is dissolved in 270 ml of THF and to this solution 70 ml of 2M ethylamine dissolved in THF is added. After the completion of the reaction the mixture is poured onto the mixture of 1N NaHSO$_4$ solution and EtOAc. The organic phase is washed with 1N NaHCO$_3$ solution. The aqueous-alkaline phase is extracted with EtOAc. The united organic phase is washed with NaCl solution and dried over Na$_2$SO$_4$. The drying material is filtered off and the filtrate is evaporated. To the resulting oil 35 mass % of water is added and the product is crystallized. 24.8 g of white bimatoprost crystals of higher than 99.5% purity are obtained.

Product:

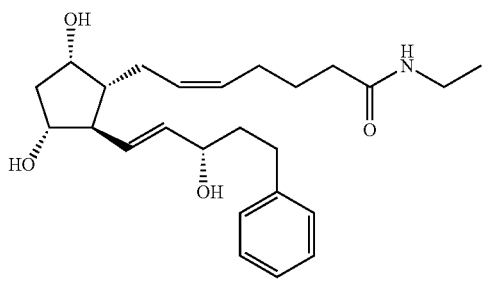

Bimatoprost
M: 415.58
$C_{25}H_{37}NO_4$

Melting point: 71.9-72.5° C.

HPLC: 99.6% bimatoprost, less than 0.3% trans-bimatoprost, 0.1% other impurity

9.) Preparation of Bimatoprost according to method iii 2.00 g of Bimatoprost acid is dissolved in 20 ml of tetrahydrofuran (THF) and at 30° C. first 1.29 g of 2-chloro-1,3-dimethylimidazolinium chloride (DMC) and 1.44 ml of triethylamine, then after 10 minutes of stirring 2.57 ml of 2M ethylamine in THF solution are added. The reaction mixture is gradually, in 1 hour, heated to 70° C. and the mixture is stirred at that temperature until the starting material disappears (approx. 1 hour). The reaction is followed by TLC.

After the completion of the reaction the mixture is poured onto the mixture of 1N NaHSO$_4$ solution and isopropyl acetate (iPrOAc). The organic phase is washed with 1N NaHCO$_3$ solution, the aqueous-alkaline phase is extracted with iPrOAc. The united organic phase is washed with NaCl solution and dried over Na$_2$SO$_4$. The drying material is filtered off and the filtrate is evaporated to obtain 1.41 g of oil.

Product:

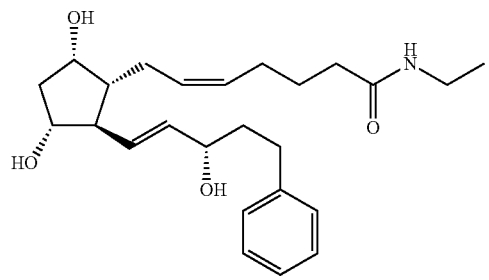

Bimatoprost
M: 415.58
$C_{25}H_{37}NO_4$

Figure 4:
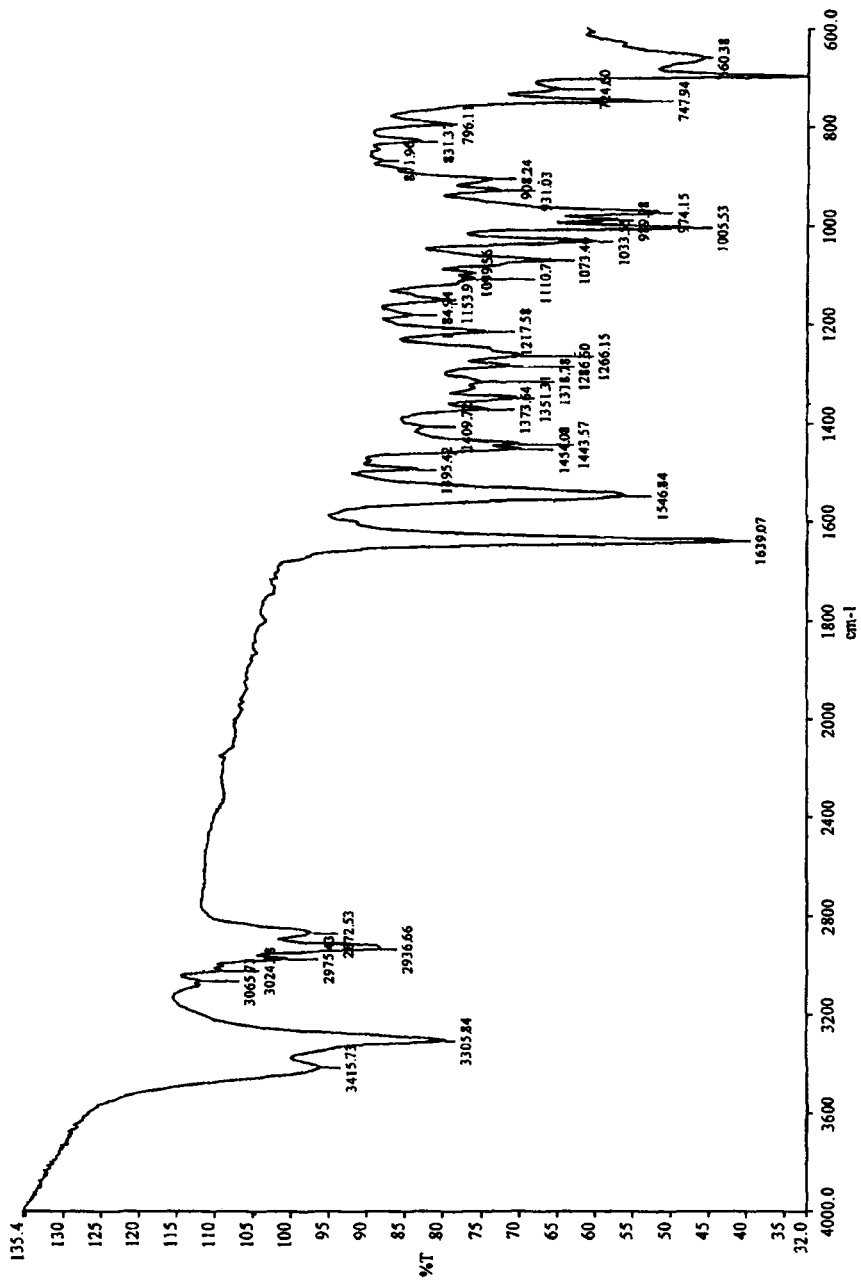
FIG. 4 presents the IR spectrum of crystal form II. obtained in the process according to the invention.
Figure 6:
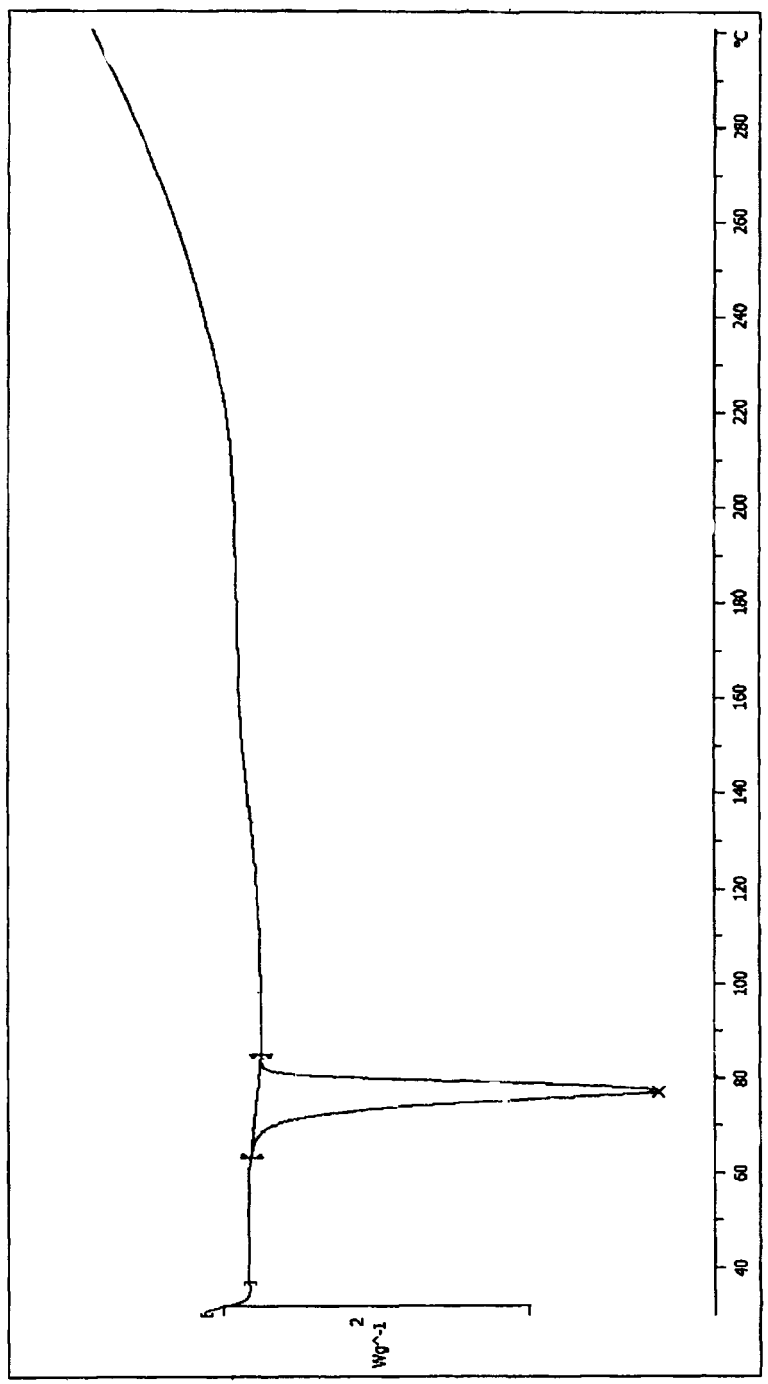
FIG. 6 presents the DSC curve of crystal form II. obtained in the process according to the invention.
Figure 8:
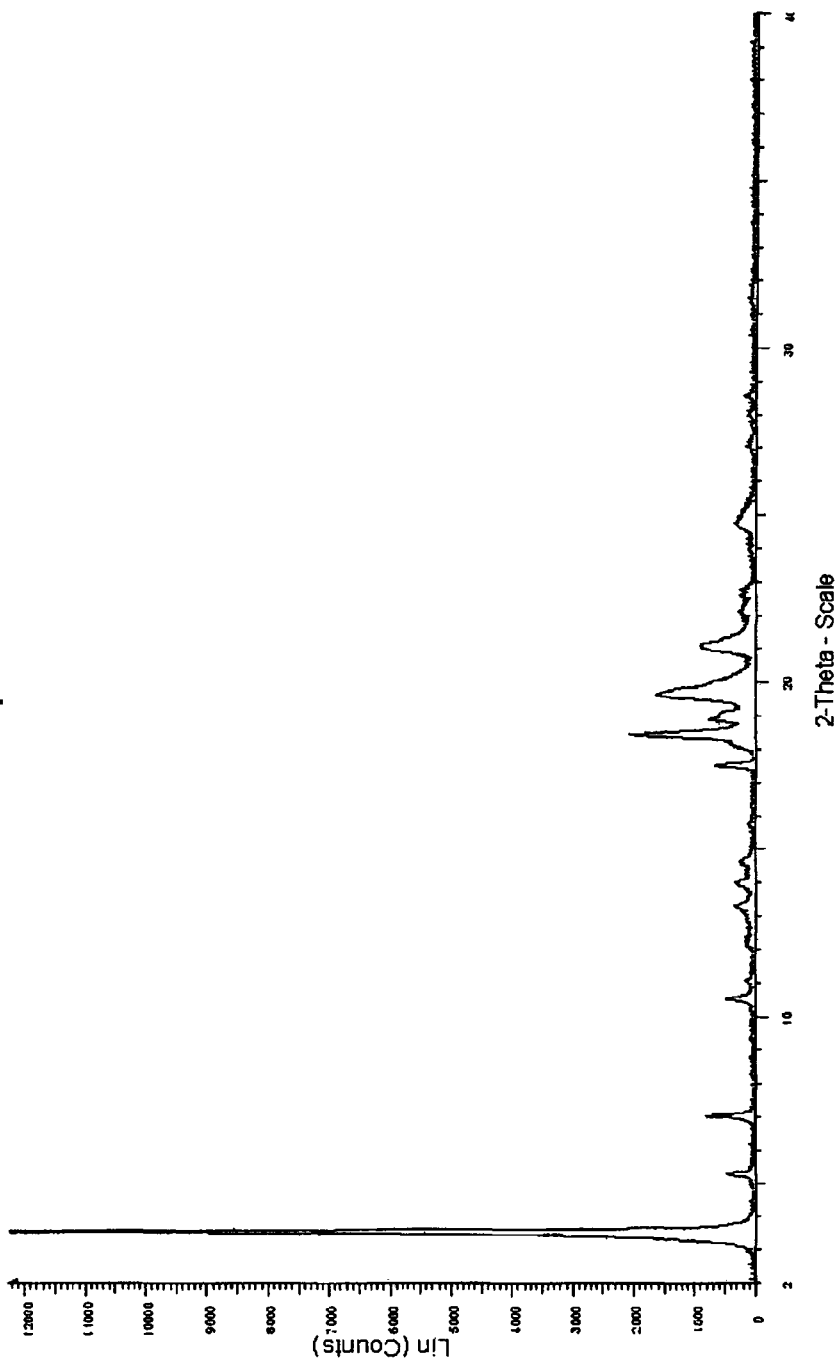
FIG. 8 presents the X-ray powder diffraction curve of crystal form II. obtained in the process according to the invention.

10.) Preparation of crystal form II. of Bimatoprost from Crude Bimatoprost Oil To the bimatoprost oil prepared according to Example 6., 35 mass % amount of purified water is added. The mixture is intensively stirred and then dried in vacuum at max. 35° C. temperature, while every 2 hour it is agitated and scratched. After complete dryness the mixture is homogenized. IR spectrum of this product is shown in FIG. 4 and the DSC curve of this product is shown in FIG. 6. The X-ray diffraction curve of produced Form II is shown in FIG. 8.
Yield: 96.9%
Mp.: 78° C.
DSC onset: 73.56° C.

11.) Preparation of Crystal Form II. of Bimatoprost

The crude bimatoprost prepared according to Example 5. is dissolved under heating in 3000-fold amount of diethyl ether. The solvent is then removed at (−)20-(−)30° C. by slowly passing through nitrogen gas. The resulting crystals are homogenized, or first exposed to mechanical effect and then homogenized.
Yield: 94.4%
Mp.: 75.9° C.
DSC onset: 72.92° C.

12.) Preparation of Crystal Form II. of Bimatoprost

To the crude bimatoprost prepared according to Example 6., 35 mass % amount of methanol is added. The mixture is intensively stirred and then dried in vacuum at max. 35° C. temperature, while every 2 hour it is agitated and scratched. After complete dryness the mixture is homogenized.
Yield: 95.8%
Mp.: 77.2° C.
DSC onset: 73.07° C.

13.) Preparation of Crystal Form II of Bimatoprost

To the crude bimatoprost prepared according to Example 6., 17.5 mass % amount of purified water and 17.5 mass % amount of ethanol are added. The mixture is intensively stirred and then dried in vacuum at max. 35° C. temperature, while every 2 hour it is agitated and scratched. After complete dryness the mixture is homogenized.
Yield: 92.3%
Mp.: 72.9° C.
DSC onset: 72.96° C.

14.)

a.) Preparation of Bimatoprost Crystal Form I.
(According to Example 38 of patent application US 20090163596)

5.2 g of crude bimatoprost is crystallized from 106 g of acetonitrile: the mixture is heated to a temperature near the boiling point, the hot solution is cooled to room temperature and the mixture is stirred at that temperature for 1 hour, then at 0-5° C. for 2 hours. The precipitated crystals are filtered off, washed with 20 g of cold (0-5° C.) acetonitrile and dried in vacuum at 0-5° C. for 1 hour, at room temperature for half an hour and at 30-40° C. for 2 hours.

Figure 3:
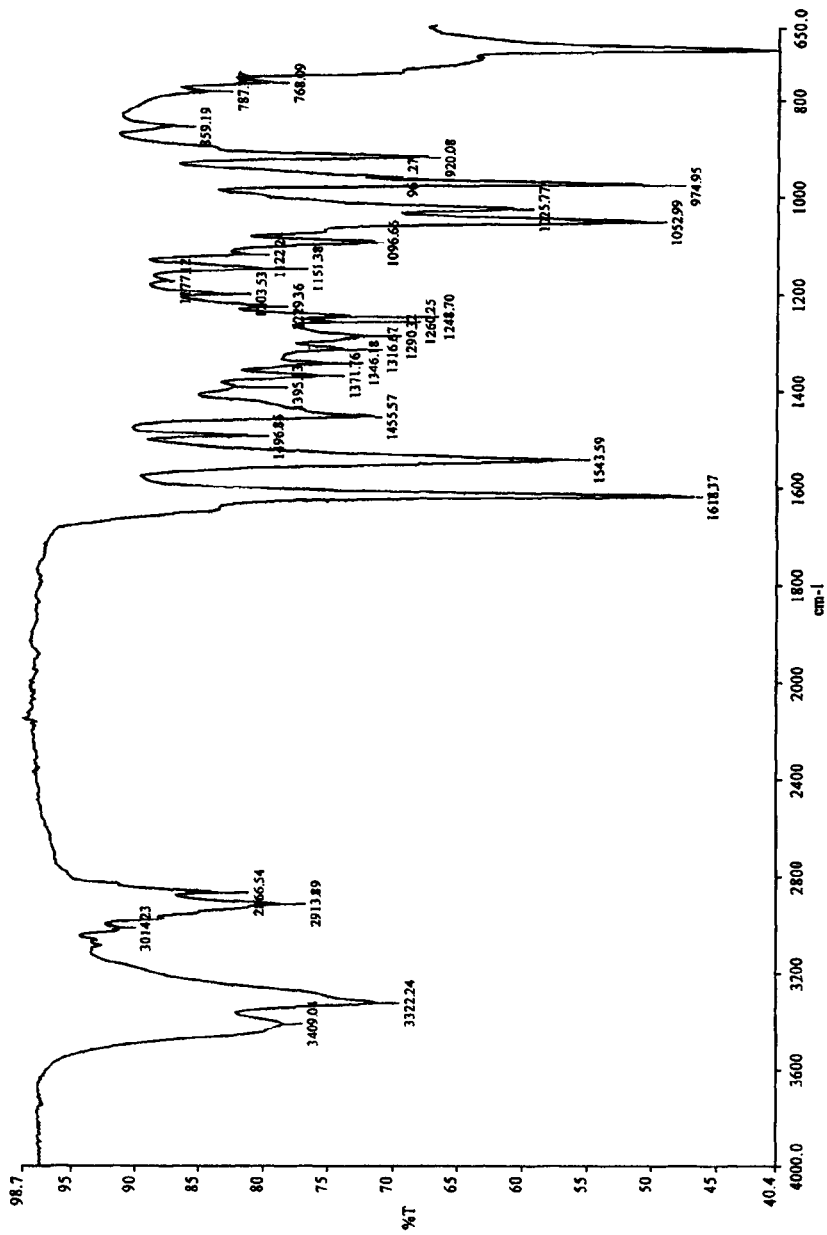
FIG. 3 presents the IR spectrum of crystal form I.
Figure 5:
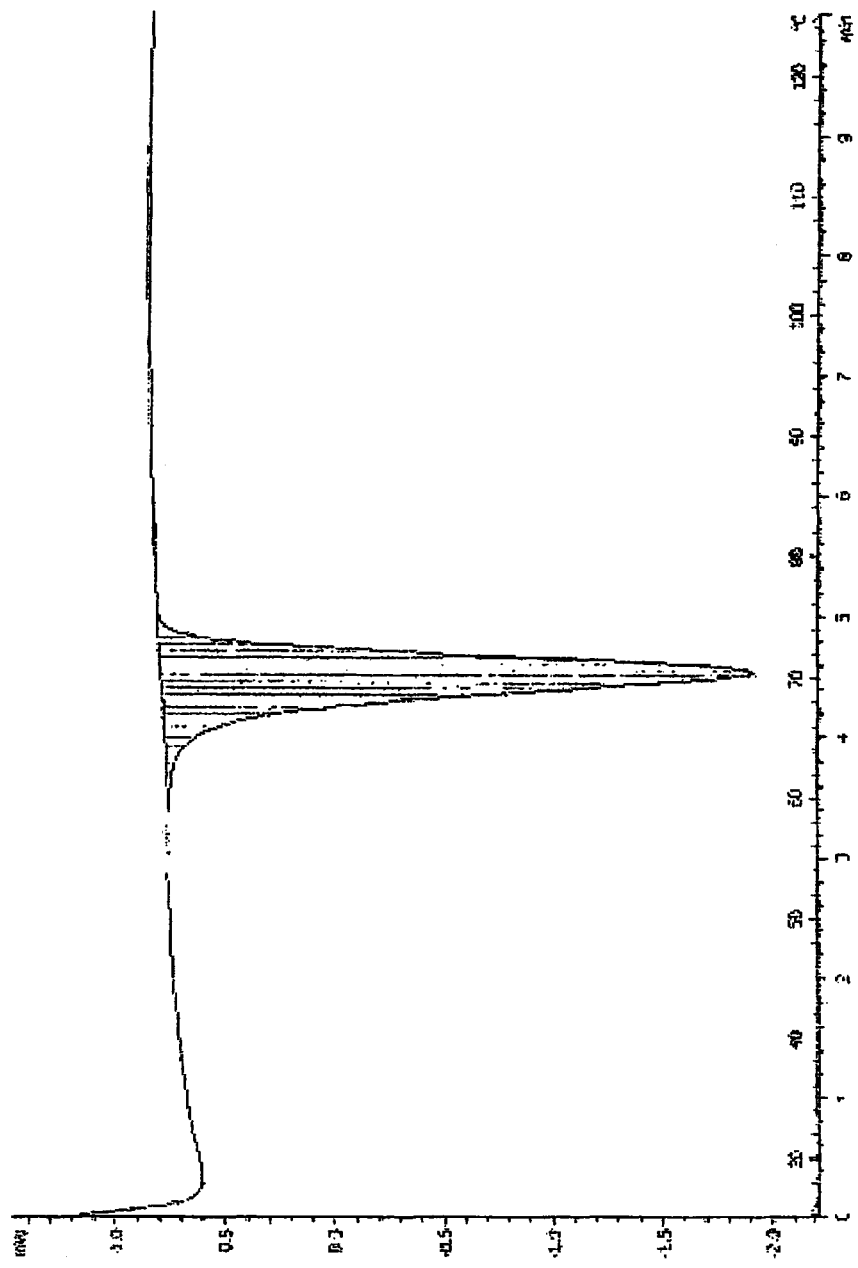
FIG. 5 presents the DSC curve of crystal form I.
Figure 7:
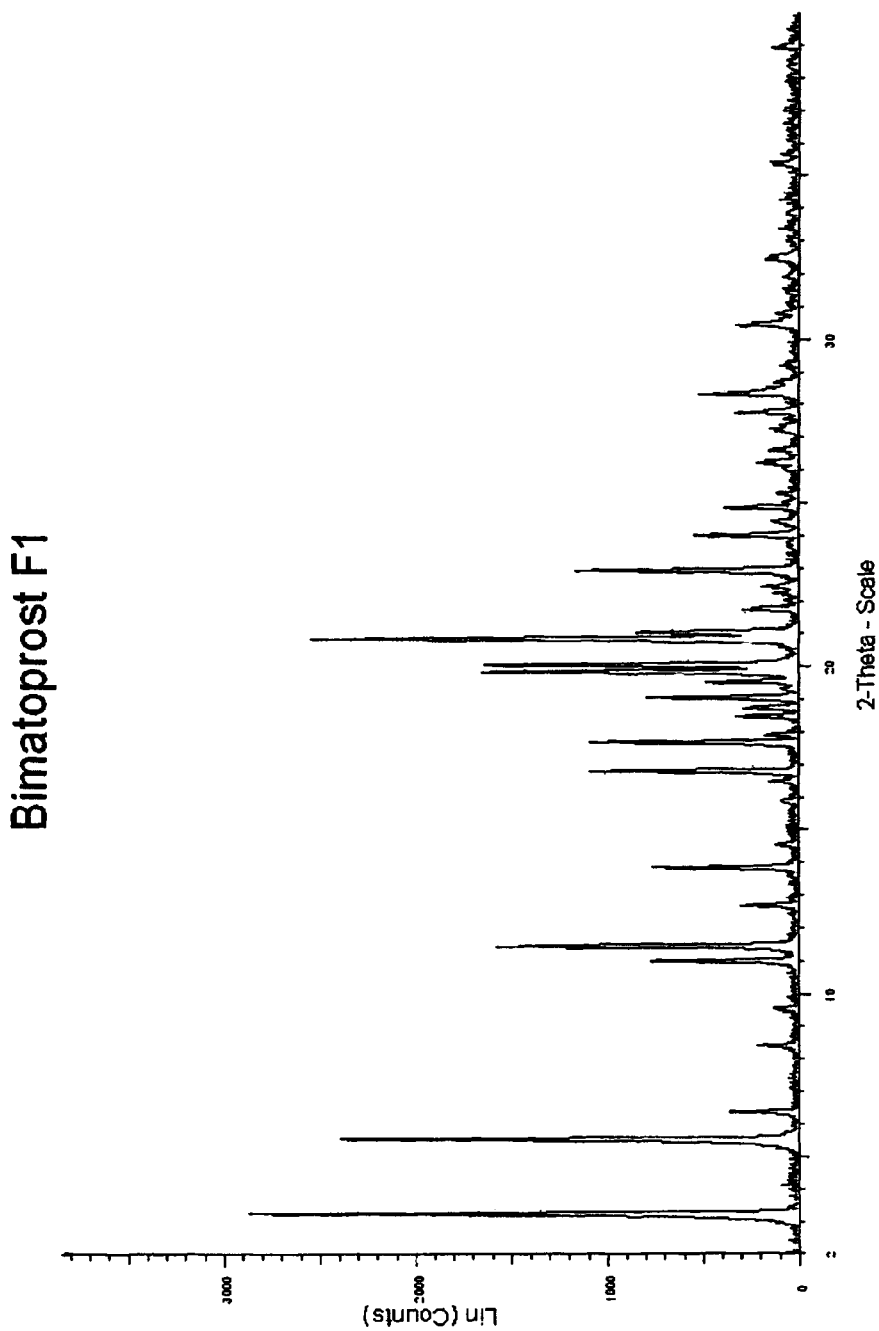
FIG. 7 presents the X-ray powder diffraction curve of crystal form I.

4.3 g of crystal form I. of bimatoprost is obtained. Its IR spectrum is shown in FIG. 3, its DSC curve is shown in FIG. 5 and its X-ray diffraction curve of Form I is shown in FIG. 7.
Yield: 83%
Mp.: 62.1° C.
DSC onset: 63.61° C.

b.) Preparation of Bimatoprost Crystal form II. Started from Form I.

To crystal form I. of bimatoprost prepared according to Example 14a., 35 mass % amount of purified water is added. The mixture is intensively stirred and then dried in vacuum at max. 35° C. temperature, while every 2 hour it is agitated and scratched. After complete dryness the mixture is homogenized.
Yield: 97.3%
Mp.: 77.7° C.
DSC onset: 73.14° C.

15.) Preparation of Crystal Form II. of a Mixture of Bimatoprost Crystal Form II. and I.

To a 50%-50% mixture of crystal form II. and I. of bimatoprost 35 mass % amount of purified water is added. The mixture is intensively stirred and then dried in vacuum at max. 35° C. temperature, while every 2 hour it is agitated and scratched. After complete dryness the mixture is homogenized.
Yield: 97.6%
Mp.: 78.2° C.
DSC onset: 73.77° C.

The invention claimed is:
1. Process for the preparation of prostaglandin amides of the general formula (I),

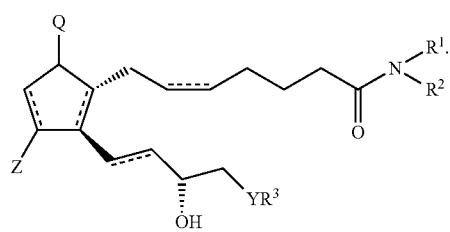

I where in the formula
the bonds marked with dotted lines may be single or double bonds, in the case of double bounds at positions 5,6 and 13,14 they may be in cis or in trans orientation,
Q represents hydroxyl-group and Z represents hydroxyl-group,
$R^1$ and $R^2$ independently represent (i) a hydrogen atom, (ii) a straight or branched $C_{1-10}$ alkyl- or aralkyl-group, optionally substituted with $-ONO_2$ group, or (iii) an aralkyl- or aryl-group, which contains heteroatom,
$R^3$ represents a phenyl group optionally substituted with an alkyl group or a halogen atom,
Y represents $(CH_2)_n$ group or O atom, and where n is 1, 2, or 3,
characterized in that an acid of the general formula (II),

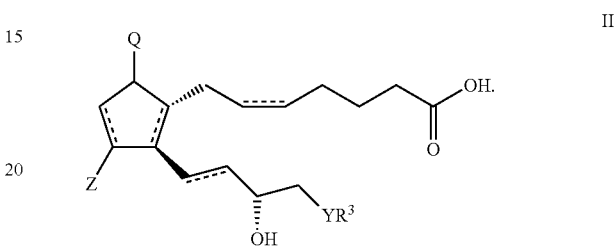

II where in the formula
the bonds marked with dotted lines may be single or double bonds, in the case of double bonds at positions 5,6 and 13,14 they may be in cis or in trans orientation,
Q represents hydroxyl-group and Z represents hydroxyl-group,
$R^3$ represents a phenyl group optionally substituted with an alkyl group or a halogen atom,
Y represents $(CH_2)_n$ group or O atom, and where n is 1, 2, or 3,
is reacted
i.) with a compound suitable to introduce group $R^4$, where $R^4$ represents a.)

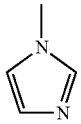

the group of formula a.)
and reacting the amide of the general formula (III), thus obtained

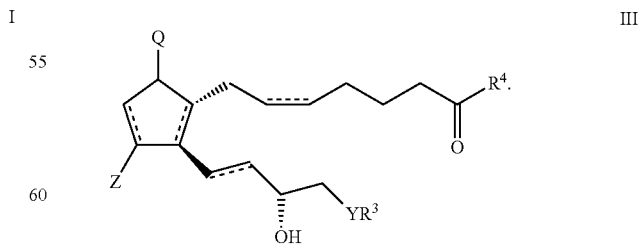

III where the meanings of Q, Z, $R^3$, $R^4$, Y and n are as defined above, with an amine of the general formula (IV)

NHR$^1$R$^2$     IV where $R^1$ and $R^2$ have the meanings as defined above, or ii.) with a compound suitable to introduce group $R^5$, where $R^5$ represents b.)
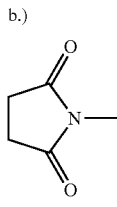

c.)
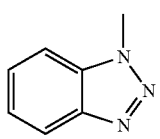

d.)
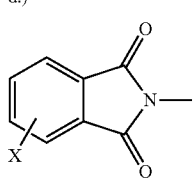

e.)
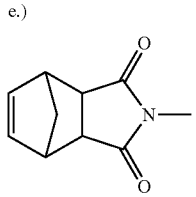

a group of formula b.), c.), d.) or e.), where (X) stands for halogen or hydrogen atom—and reacting the activated ester of the general formula (V), thus obtained

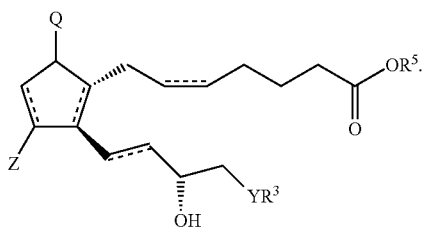

V where the meanings of Q, Z, $R^3$, $R^5$, Y and n are as defined above, with an amine of the general formula (IV), where the meanings of $R^1$ and $R^2$ are as defined above, or iii.) with an amine of the general formula (IV), —where the meanings of $R^1$ and $R^2$ are as defined above—in the presence of 2-chloro-1,3-dimethylimidazolinium chloride and a base.

2. Process according to method i.) of claim 1, characterized in that the compound suitable to introduce the group $R^4$, is 1,1'-carbonyldiimidazole or 1,1'-thiocarbonyldiimidazole.

3. Process according to method ii.) of claim 1, characterized in that for the introduction of group $R^5$, N-hydroxysuccinimide, N-hydroxyphthalimide, N-hydroxy-5-norbenendo-2,3-dicarboxamide, 1-hydroxybenzotriazole, (benzotriazol-1-yloxy)tris(dimethylamino)-phosphonium hexafluorophosphate, N,N'-disuccinimidyl carbonate or N,N'-disuccinimidyl oxalate are used, in a given case in the presence of an activating agent.

4. Process according to claim 3, characterized in that the applied activating agent is N,N'-diisopropylcarbodiimide, N,N'-dicyclohexylcarbodiimide or 2-chloro-1,3-dimethylimidazolinium chloride.

5. Process according to claim 1, characterized in that the reaction is carried out in an ether-type, or aromatic, or polar-aprotic solvent, or in the mixture of them.

6. Process according to claim 1, characterized in that the introduction of group $R^4$ is performed at a temperature between 20-80° C.

7. Process according to method i.) of claim 1, characterized in that the reaction of the compounds of formulae (III) and (IV) is carried out at a temperature between 20-80° C.

8. Process according to claim 5, wherein the process follows method ii.).

9. Process according to method ii.) of claim 1, characterized in that the introduction of group $R^5$ is carried out at a temperature between 0-80° C.

10. Process according to method ii.) of claim 1, characterized in that the reaction of the compounds of formulae (V) and (IV) is carried out at a temperature between 20-80° C.

11. Process according to methods i.) or ii.) of claim 1, characterized in that the activated carboxylic acid derivatives of formulae (III) or (V) are purified by crystallization and/or by chromatography.

12. Process according to method iii.) of claim 1, characterized in that the reaction is carried out in an ether-type or aromatic or polar-aprotic solvent, or in the mixture of them.

13. Process according to claim 5, characterized in that tetrahydrofuran is used as solvent.

14. Process according to method iii.) of claim 1, characterized in that the reaction is carried out at a temperature between 0-70° C.

15. Process according to method iii.) of claim 1, characterized in that the applied base is N-methylmorpholine, N,N-diisopropylethylamine, 1,5-diazabicyclo[4,3,0]non-5-ene or 1,8-diazabicyclo[5,4,0]undec-7-ene.

16. Process according to claim 1, characterized in that the applied base of formula (IV) is ethylamine.

17. Process according to methods i., ii or iii.) of claim 1, characterized in that the reaction is carried out under "one pot" conditions.

18. Process according to claim 1, characterized in that the introduction of group $R^4$ is performed at a temperature of 70° C.

19. Process according to method ii.) of claim 1, characterized in that the reaction of the compounds of formulae (V) and (IV) is carried out at room temperature.

* * * * *